US012805727B2

(12) United States Patent
Oberlin et al.

(10) Patent No.: US 12,805,727 B2
(45) Date of Patent: Nov. 24, 2026

(54) LASER SPECKLE FORCE FEEDBACK ESTIMATION

(71) Applicant: ACTIV Surgical, Inc., Boston, MA (US)

(72) Inventors: John Oberlin, Dorchester, MA (US); Hossein Dehghani Ashkezari, Charlestown, MA (US)

(73) Assignee: ACTIV Surgical, Inc., Boston, MA (US)

( * ) Notice: Subject to any disclaimer, the term of this patent is extended or adjusted under 35 U.S.C. 154(b) by 100 days.

(21) Appl. No.: 18/943,777

(22) Filed: Nov. 11, 2024

(65) Prior Publication Data

US 2025/0064320 A1 Feb. 27, 2025

Related U.S. Application Data

(63) Continuation of application No. 17/810,988, filed on Jul. 6, 2022, now Pat. No. 12,279,851, which is a (Continued)

(51) Int. Cl.

| | |
|---|---|
| ***A61B 5/00*** | (2006.01) |
| ***A61B 1/00*** | (2006.01) |
| ***A61B 5/026*** | (2006.01) |

(52) U.S. Cl.

CPC ...... *A61B 5/0068* (2013.01); *A61B 1/000096* (2022.02); *A61B 5/0059* (2013.01); *A61B 5/026* (2013.01); *G06T 2207/30104* (2013.01)

(58) Field of Classification Search

None

See application file for complete search history.

(56) References Cited

U.S. PATENT DOCUMENTS

| | | | |
|---|---|---|---|
| 5,768,405 | A | 6/1998 | Makram-Ebeid |
| 5,802,218 | A | 9/1998 | Braillean |

(Continued)

FOREIGN PATENT DOCUMENTS

| | | | |
|---|---|---|---|
| CN | 105303605 | B * | 10/2017 |
| CN | 108613979 | A | 10/2018 |

(Continued)

OTHER PUBLICATIONS

Briers, et al., Laser speckle contrast imaging: theoretical and practical limitations. Journal of Biomedical Optics 2013 18(6) 066018.

(Continued)

*Primary Examiner* — Gabriel I Garcia

(74) *Attorney, Agent, or Firm* — Cesari and McKenna, LLP

(57) ABSTRACT

A computer-implemented method is provided for training a neural network to determine an elastic property of a target issue region. A first training set is generated to include a plurality of sets of images. Each set of images includes a first speckle image of the target issue region at rest and a second speckle image of the target issue region being deformed by a known force. The neural network is trained in a first stage using the first training set. A second training set is generated to include the first training set and one or more sets of images having an elastic property value incorrectly determined after the first stage of training. The neural network is trained in a second stage using the second training set.

20 Claims, 12 Drawing Sheets

Related U.S. Application Data continuation of application No. PCT/US2021/012524, filed on Jan. 7, 2021.

(60) Provisional application No. 62/958,501, filed on Jan. 8, 2020.

(56) References Cited

U.S. PATENT DOCUMENTS

| | | | |
|---|---|---|---|
| 5,845,017 | A | 12/1998 | Keyes |
| 7,113,817 | B1 | 9/2006 | Winchester, Jr. |
| 7,496,395 | B2 | 2/2009 | Serov et al. |
| 8,406,859 | B2 | 3/2013 | Zuzak et al. |
| 8,668,647 | B2 | 3/2014 | Eskandari |
| 8,721,077 | B2 | 5/2014 | Vermeer et al. |
| 8,724,928 | B2 | 5/2014 | Deever |
| 8,792,098 | B2 | 7/2014 | Dewald et al. |
| 8,823,790 | B2 | 9/2014 | Dunn et al. |
| 8,891,087 | B2 | 11/2014 | Zuzak et al. |
| 9,072,445 | B2 | 7/2015 | Berguer et al. |
| 9,198,578 | B2 | 12/2015 | Zuzak et al. |
| 9,220,570 | B2 | 12/2015 | Kim et al. |
| 9,226,661 | B2 | 1/2016 | Thompson |
| 9,226,673 | B2 | 1/2016 | Ferguson, Jr. et al. |
| 9,271,658 | B2 | 3/2016 | Ferguson, Jr. et al. |
| 9,286,268 | B2 | 3/2016 | Seeman et al. |
| 9,610,021 | B2 | 4/2017 | Dvorsky |
| 9,622,662 | B2 | 4/2017 | Zuzak et al. |
| 9,788,903 | B2 | 10/2017 | Kim et al. |
| 9,962,090 | B2 | 5/2018 | DiMaio et al. |
| 10,058,256 | B2 | 8/2018 | Chen et al. |
| 10,089,737 | B2 | 10/2018 | Krieger et al. |
| 10,244,991 | B2 | 4/2019 | Shademan et al. |
| 10,265,023 | B2 | 4/2019 | Roh et al. |
| 10,278,585 | B2 | 5/2019 | Ferguson, Jr. |
| 10,390,718 | B2 | 8/2019 | Chen et al. |
| 10,398,519 | B2 | 9/2019 | Kim et al. |
| 10,600,183 | B2 | 3/2020 | Barral et al. |
| 10,675,040 | B2 | 6/2020 | Kim et al. |
| 10,722,173 | B2 | 7/2020 | Chen et al. |
| 10,792,492 | B2 | 10/2020 | Chen et al. |
| 10,948,350 | B2 | 3/2021 | Ferguson, Jr. et al. |
| 11,135,028 | B2 | 10/2021 | Kim et al. |
| 11,206,991 | B2 | 12/2021 | Oberlin et al. |
| 11,278,220 | B2 | 3/2022 | Tucker et al. |
| 11,395,590 | B2 | 7/2022 | Hamelin |
| 12,279,851 | B2 * | 4/2025 | Oberlin ................ A61B 5/0068 |
| 2002/0183601 | A1 | 12/2002 | Tearney et al. |
| 2003/0120156 | A1 | 6/2003 | Forrester et al. |
| 2004/0102686 | A1 | 5/2004 | Knudson et al. |
| 2005/0187477 | A1 | 8/2005 | Serov |
| 2009/0177098 | A1 | 7/2009 | Yakubo et al. |
| 2009/0270702 | A1 | 10/2009 | Zeng et al. |
| 2011/0112549 | A1 | 5/2011 | Neubach et al. |
| 2011/0172565 | A1 | 7/2011 | Shih et al. |
| 2011/0319775 | A1 | 12/2011 | Fujii et al. |
| 2012/0071769 | A1 | 3/2012 | Dunn |
| 2012/0095354 | A1 | 4/2012 | Dunn et al. |
| 2012/0265061 | A1 | 10/2012 | Sliwa et al. |
| 2013/0165869 | A1 | 6/2013 | Blumenkranz et al. |
| 2013/0237820 | A1 | 9/2013 | Vappou et al. |
| 2013/0274596 | A1 | 10/2013 | Azizian et al. |
| 2013/0296715 | A1 | 11/2013 | Lasser et al. |
| 2014/0132752 | A1 | 5/2014 | Edgar et al. |
| 2014/0316286 | A1 | 10/2014 | Addison et al. |
| 2015/0049178 | A1 | 2/2015 | Dunn et al. |
| 2015/0198797 | A1 | 7/2015 | Andre et al. |
| 2015/0297086 | A1 | 10/2015 | Hong et al. |
| 2016/0066832 | A1 | 3/2016 | Scanlan |
| 2016/0328848 | A1 | 11/2016 | Andre et al. |
| 2017/0017858 | A1 | 1/2017 | Roh |
| 2017/0181626 | A1 | 6/2017 | Shau et al. |
| 2017/0202607 | A1 | 7/2017 | Shelton, IV et al. |
| 2017/0319073 | A1 | 11/2017 | DiMaio |
| 2018/0025535 | A1 | 1/2018 | Lessig et al. |
| 2018/0296103 | A1 | 10/2018 | Rege et al. |
| 2019/0049354 | A1 | 2/2019 | Nadkarni |
| 2019/0167118 | A1 | 6/2019 | Vilenskii et al. |
| 2019/0167124 | A1 | 6/2019 | Verkruijsse et al. |
| 2019/0374106 | A1 | 12/2019 | Ferguson, Jr. et al. |
| 2020/0305721 | A1 | 10/2020 | Chen et al. |
| 2020/0367761 | A1 | 11/2020 | Akbari et al. |
| 2021/0030277 | A1 | 2/2021 | Ferguson, Jr. et al. |
| 2021/0145295 | A1 | 5/2021 | Fujita et al. |
| 2021/0251502 | A1 | 8/2021 | Oberlin et al. |
| 2021/0282654 | A1 | 9/2021 | Cha et al. |
| 2022/0192521 | A1 | 6/2022 | Oberlin et al. |
| 2022/0398725 | A1 | 12/2022 | Wang |
| 2023/0260141 | A1 * | 8/2023 | Schaefferkoetter .... A61B 6/032 382/131 |
| 2023/0359057 | A1 | 11/2023 | Dijkstra |

FOREIGN PATENT DOCUMENTS

| | | | |
|---|---|---|---|
| CN | 110301908 | A | 10/2019 |
| WO | WO-2000058775 | A1 | 5/2000 |
| WO | WO-2010096447 | A2 | 8/2010 |
| WO | WO-2010096453 | A1 | 8/2010 |
| WO | WO-2012096878 | A2 | 7/2012 |
| WO | WO-2014152753 | A1 | 9/2014 |
| WO | WO-2016061052 | A1 | 4/2016 |
| WO | WO-2016153741 | A1 | 9/2016 |
| WO | WO-2017075602 | A1 | 5/2017 |
| WO | WO-207139774 | A1 | 8/2017 |
| WO | WO-2018029123 | A1 | 2/2018 |
| WO | WO-2019045971 | A1 | 3/2019 |
| WO | WO-2019237013 | A1 | 12/2019 |
| WO | WO-2020006454 | A1 | 1/2020 |
| WO | WO-2021142138 | A1 | 7/2021 |
| WO | WO-2021163603 | A1 | 8/2021 |
| WO | WO-2022029308 | A1 | 2/2022 |
| WO | WO-2022058499 | A1 | 3/2022 |
| WO | WO-2023049401 | A1 | 3/2023 |

OTHER PUBLICATIONS

Draijer, et al., Review of laser speckle contrast techniques for visualizing tissue perfusion. Lasers Med Sci 2009 24:639-651.

Duncan, et al., Statistics of Local Speckle Contrast. Journal of the Optical Society of America, A. V. 25, pp. 9-15 (2008).

Dunn, et al. Laser speckle contrast imaging in biomedical optics. Journal of Biomedical Optics 15(1), 011109 (Jan./Feb. 2010).

Holstein-Rathlou et al. Nephron blood flow dynamics measured by laser speckle contrast imaging. Am J Physiol Renal Physiol 300: F319-F329, 2011.

Humeau-Heurtier, et al., "Multiscale Entropy Study of Medical Laser Speckle Contrast Images" IEEE Transactions on Biomedicalengineering, vol. 60, No. 3, Mar. 2013 (Year: 2013).

Jain, et al., Measuring light transport properties using speckle pattern structured illumination. Nature Scientific Reports 2019 9:11157. https://doi.org/10.1038/s41598-019-47256-8.

Kalchenko, et al., A robust method for adjustment of laser speckle contrast imaging during transcranial mouse brain visualization. Photonics 2019, 6(80); doi:10.3390/photonics6030080.

PCT/US2022/044608 International Search Report and Written Opinion dated Jan. 18, 2023.

PCT/US21/12524 International Search Report and Written Opinion dated Jun. 2, 2021.

PCT/US21/18008 International Search Report and Written Opinion dated Jun. 23, 2021.

Postnikov, et al., Gaussian sliding window for robust processing laser speckle contrast images. Int J Numer Meth Biomed Engng 2019; 35:e3186. http://doi.org/10.1002/cnm.3186.

Ramirez-San-Juan et al., Spatial versus temporal laser speckle contrast analyses in the presence of static optical scatterers. Journal of Biomedical Optics 2014 19(10).

Richards et al. Intraoperative laser speckle contrast imaging with retrospective motion correction for quantitative assessment of cerebral blood flow. Neurophotonics 1(1), 015006 (Jul.-Sep. 2014).

Richards et al. Low-cost laser speckle contrast imaging of blood flow using a webcam. 2013 Optical Society of America.

(56) References Cited

OTHER PUBLICATIONS

Song et al., Effect of signal intensity and camera quantization on laser speckle contrast analysis. Biomedical Optics Express 2013. vol. 4, No. 1.
U.S. Appl. No. 17/245,374 Notice of Allowance dated Nov. 10, 2021.
U.S. Appl. No. 17/245,374 Notice of Allowance dated Oct. 28, 2021.
U.S. Appl. No. 17/245,374 Office Action dated Jul. 13, 2021.
Vaz, et al., Laser Speckle Imaging to Monitor Microvascular Blood Flow: A Review, IEEE Reviews In Biomedical Engineering, vol. 9,2016 (Year: 2016).
EP21738084.9 Extended European Search Report dated Feb. 5, 2024.
EP21754452.7 Partial Supplementary European Search Report dated Feb. 20, 2024.
Hajjarian Z. et al. "Measurement of bulk mechanical properties of tissue using laser speckle rheology", Engineering in Medicine and Biology Society, EMBC, Aug. 30, 2011, pp. 5746-5748.
PCT/US/2022/044608 Application—International Search Report and Written Opinion, Jan. 18, 2023, 18 pages.
Parthasarathy, et al. "Laser speckle contrast imaging of cerebral blood flow in humans during neurosurgery: a piolot clinical study" J Biomed Opt. Nov.-Dec. 2010, 8 pages.
Zakharov, Pavel, Frank Scheffold, and Bruno Weber. "Laser speckle analysis synchronised with cardiac cycle." *European Conference on Biomedical Optics*. Optica Publishing Group, 2015.
Hwang, Wonjun, and Soo-Chul Lim. "Inferring interaction force from visual information without using physical force sensors." Sensors 17.11 (2017): 2455.

* cited by examiner

LASER SPECKLE FORCE FEEDBACK ESTIMATION

CROSS-REFERENCE

The present application is a continuation of U.S. patent application Ser. No. 17/810,988, entitled LASER SPECKLE FORCE FEEDBACK ESTIMATION, filed on Jul. 6, 2022 by John Oberlin et al., which is a continuation of International Patent Application No. PCT/US21/12524, filed on Jan. 7, 2021, which claims priority to U.S. Provisional Patent Application No. 62/958,501 filed on Jan. 8, 2020, each of which is incorporated herein by reference in its entirety.

BACKGROUND

While the increased prevalence of machine operated and telemedical surgery robots has enabled significant treatment advances through their high precision and low requisite incision areas, many such systems are unable to provide caregivers with tactile feedback. Such tactile feedback is often useful to determine critical structures during surgery.

SUMMARY

Provided herein is a computer-implemented method for determining an estimated force applied on a target tissue region, the method comprising: obtaining a set of images of the target tissue region; determining a perfusion property, a set of spatial measurement, or both of the target tissue region based at least on the set of images; determining a deformation of the target tissue region based at least on the set of spatial measurements; determining a viscoelastic property of the target tissue region based at least on the deformation of the target tissue region, the perfusion property of the target tissue region, or both; and determining the estimated force applied on the target tissue region based at least on the viscoelastic property of the target tissue region.

In some embodiments, the set of images comprises a laser speckle image, an RGB image, an RGB-Depth image, or any combination thereof. In some embodiments, the laser speckle image is a subjective laser speckle image, an objective laser speckle image, a near-field laser speckle image, or any combination thereof. In some embodiments, the set of images is obtained while emitting two or more different wavelengths of light at the target tissue region.

In some embodiments, the set of images is obtained while emitting light at the target tissue region having a number of different wavelengths of about 10 to about 1,000. In some embodiments, the set of images is obtained while emitting light at the target tissue region having a number of different wavelengths of about 10 to about 50, about 10 to about 100, about 10 to about 200, about 10 to about 300, about 10 to about 400, about 10 to about 500, about 10 to about 600, about 10 to about 700, about 10 to about 800, about 10 to about 900, about 10 to about 1,000, about 50 to about 100, about 50 to about 200, about 50 to about 300, about 50 to about 400, about 50 to about 500, about 50 to about 600, about 50 to about 700, about 50 to about 800, about 50 to about 900, about 50 to about 1,000, about 100 to about 200, about 100 to about 300, about 100 to about 400, about 100 to about 500, about 100 to about 600, about 100 to about 700, about 100 to about 800, about 100 to about 900, about 100 to about 1,000, about 200 to about 300, about 200 to about 400, about 200 to about 500, about 200 to about 600, about 200 to about 700, about 200 to about 800, about 200 to about 900, about 200 to about 1,000, about 300 to about 400, about 300 to about 500, about 300 to about 600, about 300 to about 700, about 300 to about 800, about 300 to about 900, about 300 to about 1,000, about 400 to about 500, about 400 to about 600, about 400 to about 700, about 400 to about 800, about 400 to about 900, about 400 to about 1,000, about 500 to about 600, about 500 to about 700, about 500 to about 800, about 500 to about 900, about 500 to about 1,000, about 600 to about 700, about 600 to about 800, about 600 to about 900, about 600 to about 1,000, about 700 to about 800, about 700 to about 900, about 700 to about 1,000, about 800 to about 900, about 800 to about 1,000, or about 900 to about 1,000. In some embodiments, the set of images is obtained while emitting light at the target tissue region having a number of different wavelengths of about 10, about 50, about 100, about 200, about 300, about 400, about 500, about 600, about 700, about 800, about 900, or about 1,000. In some embodiments, the set of images is obtained while emitting light at the target tissue region having a number of different wavelengths of at least about 10, about 50, about 100, about 200, about 300, about 400, about 500, about 600, about 700, about 800, or about 900. In some embodiments, the set of images is obtained while emitting light at the target tissue region having a number of different wavelengths of at most about 50, about 100, about 200, about 300, about 400, about 500, about 600, about 700, about 800, about 900, or about 1,000.

In some embodiments, the set of images of the target issue region and the set spatial measurements of the target tissue region are obtained simultaneously in real time as the target issue region undergoes the deformation. In some embodiments, the set of images of the target issue region is obtained in-vitro. In some embodiments, the set of images of the target issue region is obtained in-vivo. In some embodiments, at least one of the set of images of the target issue region is obtained while the target tissue region undergoes a known deformation by a pre-determined force. In some embodiments, the target tissue region is a soft tissue region. In some embodiments, determining the mechanical property, the viscoelastic property, or both of the target tissue region is performed by a machine learning algorithm. In some embodiments, the viscoelastic property comprises a viscous property, an elastic property, a fluid mechanics property, or any combination thereof. In some embodiments, the method further comprises obtaining depth measurements from a depth sensor, and wherein the deformation of the target tissue region is further based on the depth measurements. In some embodiments, the spatial measurements are one-dimensional, two-dimensional, or three-dimensional. In some embodiments, the depth sensor comprises a stereo camera, a video camera, a time of flight sensor, or any combination thereof. In some embodiments, the deformation of the target tissue region comprises a one-dimensional deformation, a two-dimensional deformation, a three-dimensional deformation, or any combination thereof. In some embodiments, determining the estimated force applied to the target tissue region is performed by a machine learning algorithm. In some embodiments, the force is applied by a human operator, and wherein the method further comprises providing a feedback to the operator based on the determined estimated force applied on the target tissue region. In some embodiments, the feedback comprises a visual feedback, an auditory feedback, a haptic feedback, or any combination thereof. In some embodiments, the visual feedback comprises a color coded visual feedback, a displayed value, a map, or any combination thereof corresponding to the estimated force. In some embodiments, a relationship between the estimated force and the feedback is linear, non-linear, or exponential. In some embodiments, the force is applied by an autonomous or semi-autonomous device, and wherein the method further comprises providing a control feedback to the autonomous or semi-autonomous device based on the force applied by the deformed tissue. In some embodiments, the autonomous or semi-autonomous device alters its treatment based on the control feedback. In some embodiments, the method further comprises determining a fluid flow rate within the target tissue based at least on (i) the set of images, (ii) the spatial measurements, (iii) the viscoelastic property of the target tissue region, (iv) the deformation of the target tissue region, or any combination thereof. In some embodiments, the fluid is blood, sweat, semen, saliva, pus, urine, air, mucus, milk, bile, a hormone, or any combination thereof. In some embodiments, the fluid flow rate within the target tissue is determined by a machine learning algorithm. In some embodiments, the fluid flow rate is determined by a machine learning algorithm. In some embodiments, the method further comprises determining an identification of the target tissue based at least on (i) the set of images, (ii) the spatial measurements, (iii) the viscoelastic property of the target tissue region, (iv) the deformation of the target tissue region, or any combination thereof. In some embodiments, the identification of the target tissue is determined by a machine learning algorithm. In some embodiments, the identification of the target tissue is an identification that the target tissue is cancerous, benign, malignant, or healthy.

Another aspect provided herein is a computer-implemented system comprising: a digital processing device comprising: at least one processor, an operating system configured to perform executable instructions, a memory, and a computer program including instructions executable by the digital processing device to create an application for determining an estimated force applied on a target tissue region, the application comprising: a module obtaining a set of images of the target tissue region; a module determining a perfusion property, a set of spatial measurement, or both of the target tissue region based at least on the set of images; a module determining a deformation of the target tissue region based at least on the set of spatial measurements; a module determining a viscoelastic property of the target tissue region based at least on the deformation of the target tissue region, the perfusion property of the target tissue region, or both; and a module determining the estimated force applied on the target tissue region based at least on the viscoelastic property of the target tissue region.

In some embodiments, the set of images comprises a laser speckle image, an RGB image, an RGB-Depth image, or any combination thereof. In some embodiments, the laser speckle image is a subjective laser speckle image, an objective laser speckle image, a near-field laser speckle image, or any combination thereof. In some embodiments, the set of images is obtained while emitting two or more different wavelengths of light at the target tissue region. In some embodiments, the set of images is obtained while emitting about 10 to about 1,000 different wavelengths of light at the target tissue region. In some embodiments, the set of images of the target issue region and the set spatial measurements of the target tissue region are obtained simultaneously in real time as the target issue region undergoes the deformation. In some embodiments, the set of images of the target issue region is obtained in-vitro. In some embodiments, the set of images of the target issue region is obtained in-vivo. In some embodiments, at least one of the set of images of the target issue region is obtained while the target tissue region undergoes a known deformation by a pre-determined force. In some embodiments, the target tissue region is a soft tissue region. In some embodiments, determining the mechanical property, the viscoelastic property, or both of the target tissue region is performed by a machine learning algorithm. In some embodiments, the viscoelastic property comprises a viscous property, an elastic property, a fluid mechanics property, or any combination thereof. In some embodiments, the application further comprises a module obtaining depth measurements from a depth sensor, and wherein the deformation of the target tissue region is further based on the depth measurements. In some embodiments, the spatial measurements are one-dimensional, two-dimensional, or three-dimensional. In some embodiments, the depth sensor comprises a stereo camera, a video camera, a time of flight sensor, or any combination thereof. In some embodiments, the deformation of the target tissue region comprises a one-dimensional deformation, a two-dimensional deformation, a three-dimensional deformation, or any combination thereof. In some embodiments, determining the estimated force applied to the target tissue region is performed by a machine learning algorithm. In some embodiments, the force is applied by a human operator, and wherein the application further comprises a module providing a feedback to the operator based on the determined estimated force applied on the target tissue region. In some embodiments, the feedback comprises a visual feedback, an auditory feedback, a haptic feedback, or any combination thereof. In some embodiments, the visual feedback comprises a color coded visual feedback, a displayed value, a map, or any combination thereof corresponding to the estimated force. In some embodiments, a relationship between the estimated force and the feedback is linear, non-linear, or exponential. In some embodiments, the force is applied by an autonomous or semi-autonomous device, and wherein the application further comprises a module providing a control feedback to the autonomous or semi-autonomous device based on the force applied by the deformed tissue. In some embodiments, the autonomous or semi-autonomous device alters its treatment based on the control feedback. In some embodiments, the application further comprising a module determining a fluid flow rate within the target tissue based at least on (i) the set of images, (ii) the spatial measurements, (iii) the viscoelastic property of the target tissue region, (iv) the deformation of the target tissue region, or any combination thereof. In some embodiments, the fluid is blood, sweat, semen, saliva, pus, urine, air, mucus, milk, bile, a hormone, or any combination thereof. In some embodiments, the fluid flow rate within the target tissue is determined by a machine learning algorithm. In some embodiments, the fluid flow rate is determined by a machine learning algorithm. In some embodiments, the application further comprising a module determining an identification of the target tissue based at least on (i) the set of images, (ii) the spatial measurements, (iii) the viscoelastic property of the target tissue region, (iv) the deformation of the target tissue region, or any combination thereof. In some embodiments, the identification of the target tissue is determined by a machine learning algorithm. In some embodiments, the identification of the target tissue is an identification that the target tissue is cancerous, benign, malignant, or healthy.

Another aspect provided herein is a non-transitory computer-readable storage media encoded with a computer program including instructions executable by a processor to create an application for determining an estimated force applied on a target tissue region, the application comprising: a module obtaining a set of images of the target tissue region; a module determining a perfusion property, a set of spatial measurement, or both of the target tissue region based at least on the set of images; a module determining a deformation of the target tissue region based at least on the set of spatial measurements; a module determining a viscoelastic property of the target tissue region based at least on the deformation of the target tissue region, the perfusion property of the target tissue region, or both; and a module determining the estimated force applied on the target tissue region based at least on the viscoelastic property of the target tissue region.

In some embodiments, the set of images comprises a laser speckle image, an RGB image, an RGB-Depth image, or any combination thereof. In some embodiments, the laser speckle image is a subjective laser speckle image, an objective laser speckle image, a near-field laser speckle image, or any combination thereof. In some embodiments, the set of images is obtained while emitting two or more different wavelengths of light at the target tissue region. In some embodiments, the set of images is obtained while emitting about 10 to about 1,000 different wavelengths of light at the target tissue region. In some embodiments, the set of images of the target issue region and the set spatial measurements of the target tissue region are obtained simultaneously in real time as the target issue region undergoes the deformation. In some embodiments, the set of images of the target issue region is obtained in-vitro. In some embodiments, the set of images of the target issue region is obtained in-vivo. In some embodiments, at least one of the set of images of the target issue region is obtained while the target tissue region undergoes a known deformation by a pre-determined force. In some embodiments, the target tissue region is a soft tissue region. In some embodiments, determining the mechanical property, the viscoelastic property, or both of the target tissue region is performed by a machine learning algorithm. In some embodiments, the viscoelastic property comprises a viscous property, an clastic property, a fluid mechanics property, or any combination thereof. In some embodiments, the application further comprises a module obtaining depth measurements from a depth sensor, and wherein the deformation of the target tissue region is further based on the depth measurements. In some embodiments, the spatial measurements are one-dimensional, two-dimensional, or three-dimensional. In some embodiments, the depth sensor comprises a stereo camera, a video camera, a time of flight sensor, or any combination thereof. In some embodiments, the deformation of the target tissue region comprises a one-dimensional deformation, a two-dimensional deformation, a three-dimensional deformation, or any combination thereof. In some embodiments, determining the estimated force applied to the target tissue region is performed by a machine learning algorithm. In some embodiments, the force is applied by a human operator, and wherein the application further comprises a module providing a feedback to the operator based on the determined estimated force applied on the target tissue region. In some embodiments, the feedback comprises a visual feedback, an auditory feedback, a haptic feedback, or any combination thereof. In some embodiments, the visual feedback comprises a color coded visual feedback, a displayed value, a map, or any combination thereof corresponding to the estimated force. In some embodiments, a relationship between the estimated force and the feedback is linear, non-linear, or exponential. In some embodiments, the force is applied by an autonomous or semi-autonomous device, and wherein the application further comprises a module providing a control feedback to the autonomous or semi-autonomous device based on the force applied by the deformed tissue. In some embodiments, the autonomous or semi-autonomous device alters its treatment based on the control feedback. In some embodiments, the application further comprises a module determining a fluid flow rate within the target tissue based at least on (i) the set of images, (ii) the spatial measurements, (iii) the viscoelastic property of the target tissue region, (iv) the deformation of the target tissue region, or any combination thereof. In some embodiments, the fluid is blood, sweat, semen, saliva, pus, urine, air, mucus, milk, bile, a hormone, or any combination thereof. In some embodiments, the fluid flow rate within the target tissue is determined by a machine learning algorithm. In some embodiments, the fluid flow rate is determined by a machine learning algorithm. In some embodiments, the application further comprising a module determining an identification of the target tissue based at least on (i) the set of images, (ii) the spatial measurements, (iii) the viscoelastic property of the target tissue region, (iv) the deformation of the target tissue region, or any combination thereof. In some embodiments, the identification of the target tissue is determined by a machine learning algorithm. In some embodiments, the identification of the target tissue is an identification that the target tissue is cancerous, benign, malignant, or healthy.

Another aspect provided herein is a computer-implemented method for training a neural network to determine an elastic property of a target issue region, the method comprising: generating a first training set comprising a plurality of sets of set of images, wherein each set of images comprises a first speckle image of the target issue region at rest and a second speckle image of the target issue region being deformed by a known force; training the neural network in a first stage using the first training set; generating a second training set comprising the first training set and the sets of set of images whose elastic property value was incorrectly determined after the first stage of training; and training the neural network in a second stage using the second training set. In some embodiments, the set of images comprises a subjective set of images, an objective set of images, a near-field set of images, or any combination thereof. In some embodiments, the set of images is obtained while emitting at least 10 different wavelengths of light at the target tissue region. In some embodiments, the set of images is obtained while emitting about 10 to about 1,000 different wavelengths of light at the target tissue region. In some embodiments, the viscoelastic property comprises a viscous property, an elastic property, a fluid mechanics property, or any combination thereof. In some embodiments, the spatial measurements are one-dimensional, two-dimensional, or three-dimensional.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 8B shows an image of a sample tissue region injected with an;

DETAILED DESCRIPTION

As machine operated and telemedical surgery robots and mechanisms are unable to provide caregivers with tactile feedback, there is an unmet need for systems, methods, and media capable of determining mechanical properties of target tissues to enable such feedback. The present disclosure addresses at least the above need.

Method, Systems and Media for Determining an Estimated Force

Figure 1:
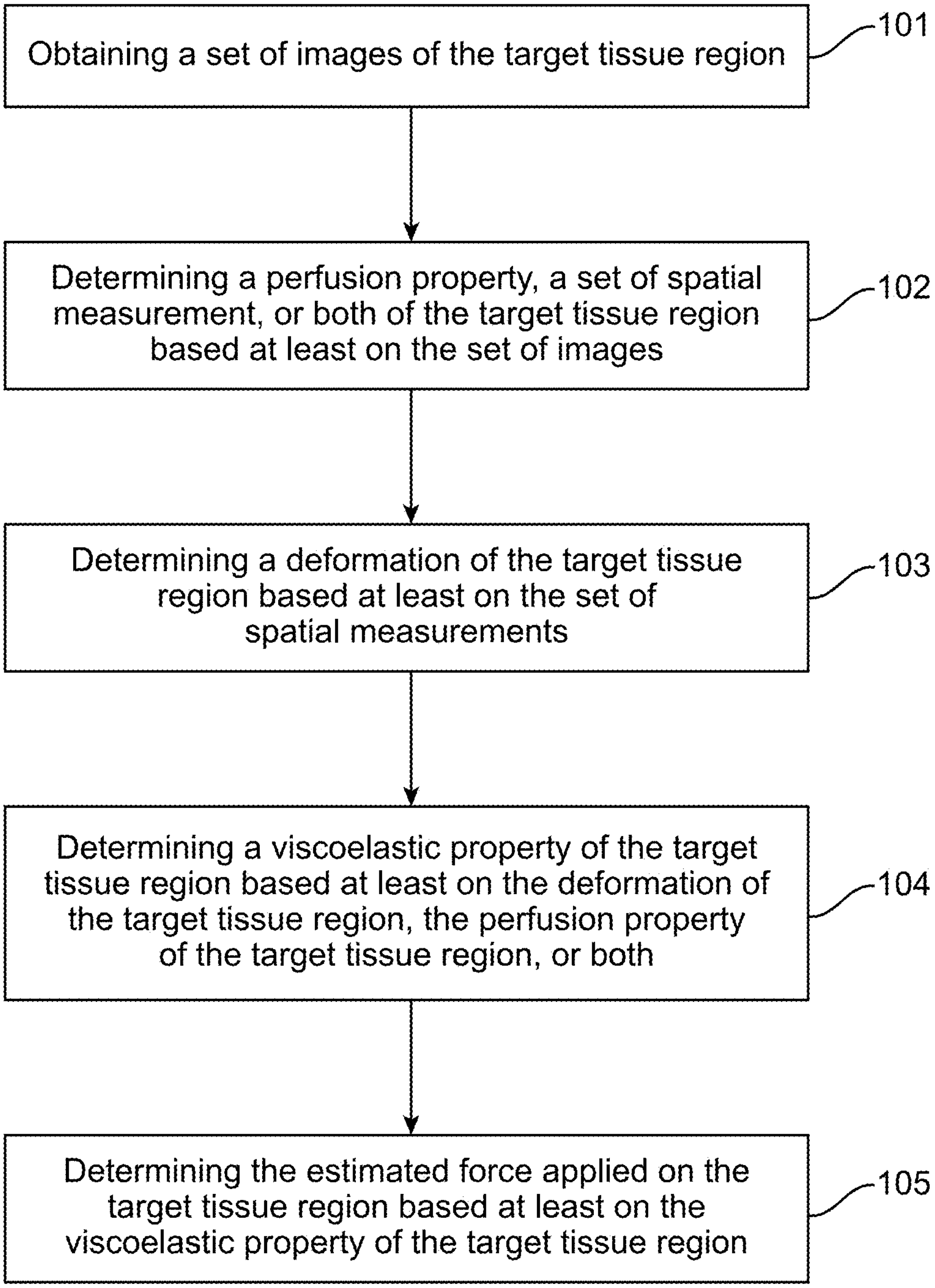
FIG. 1 shows a schematic diagram of a method for determining an estimated force, per an embodiment herein.

Provided herein is a computer-implemented method, systems and media for determining an estimated force applied on a target tissue region. In some embodiments, per FIG. 1, the method comprises: obtaining a set of images of the target tissue region 101; determining a perfusion property, a set of spatial measurement, or both of the target tissue region 102; determining a deformation of the target tissue region 103; determining a viscoelastic property of the target tissue region 104; and determining the estimated force applied on the target tissue region 105. In some embodiments, the estimated force applied on the target tissue region is determined based at least on the viscoelastic property of the target tissue region.

In some embodiments, the target tissue is a soft tissue. In some embodiments, the target tissue is an epithelial tissue, connective tissue, muscular tissue, nervous tissue, or any combination thereof. In some embodiments, the target tissue region is a treatment region receiving treatment by a caregiver. In some embodiments, the target tissue region has an area of about 2 $mm^2$, 5 $mm^2$, 10 $mm^2$, 20 $mm^2$, 50 $mm^2$, 100 $mm^2$, 200 $mm^2$, 500 $mm^2$, 1,000 $mm^2$, 10,000 $mm^2$, 100,000 $mm^2$, 1,000,000 $mm^2$, or more including increments therein. In some embodiments, the target tissue is in-vitro. In some embodiments, the target tissue is in-vivo.

Perfusion Property

Figure 8A:
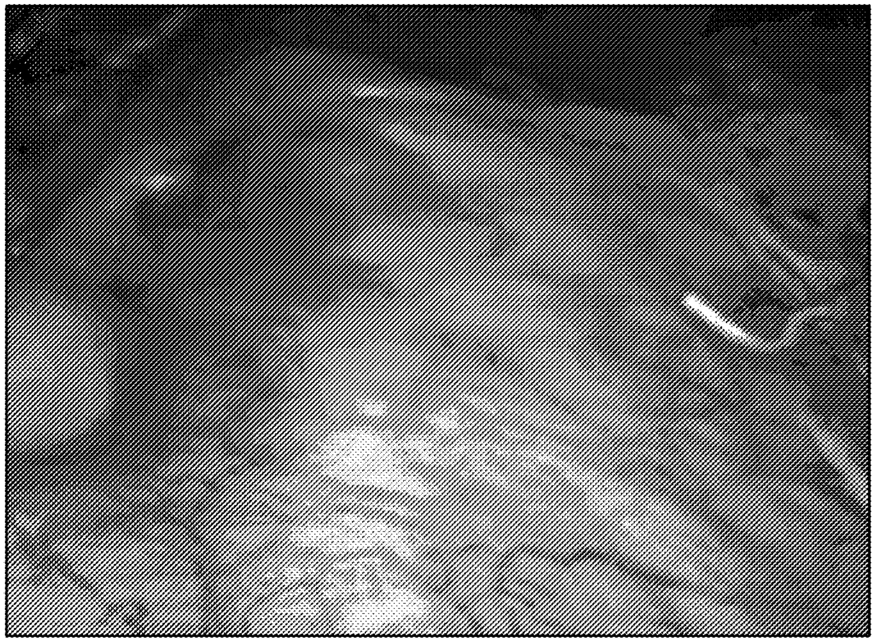
FIG. 8A (PRIOR ART)
FIG. 8A shows an image of a sample tissue region.
Figure 8B:
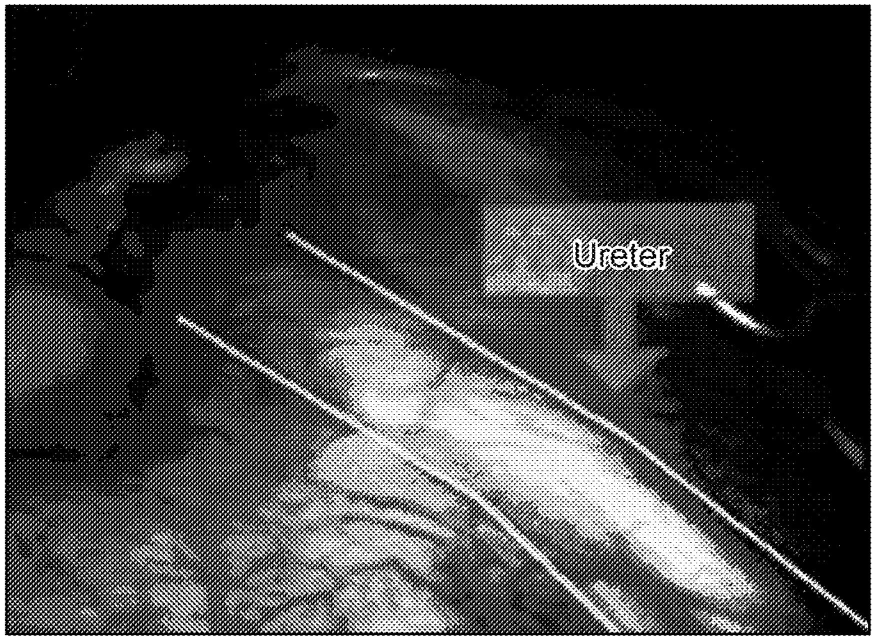
FIG. 8B (PRIOR ART)

Current methods of determining perfusion in a target tissue, per FIGS. 8A and 8B, typically require the infusion of a fluorescent dye (e.g. an indocyanine green (ICG) dye) into a patient. While key perfusion structures are visible in FIG. 8B, such infusions have several shortcomings. First as the dye requires about 5 minutes to about 24 hours to reach the target tissue, such a procedure must be planned before a surgery of the target tissue, and/or delay the visualization effects. Any additional planning and treatment steps that could go awry should be avoided to ensure a successful surgery. Such a large dye visualization variation among patients further encumbers its use. Further, as clinicians are charged per dosage of the dye, mistimed or untimely injections are costly. Second, the visualization capabilities of the dye dissipate as it flows through the bloodstream, leaving a very narrow opportunity of use. Finally, such dyes are not indicated for all patients based on their biologic interactions.

By contrast, in some embodiments, the methods, systems, and media herein do not require the use of a dye or other injected visualization medium. Further the methods, systems, and media herein require little to no planning for use, can be used instantly without any waiting periods, and can be used continually throughout a surgery without inducing extra costs or procedures.

Figure 10A:
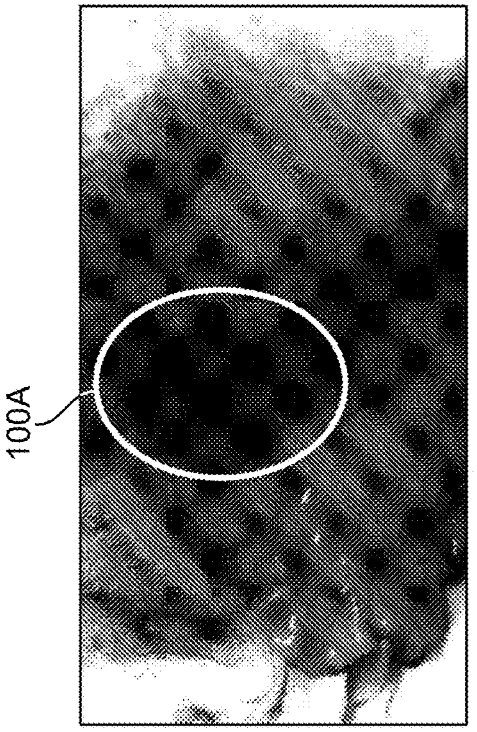
FIG. 10A shows an image of an unablated target tissue region injected with the ICG dye.
Figure 10B:
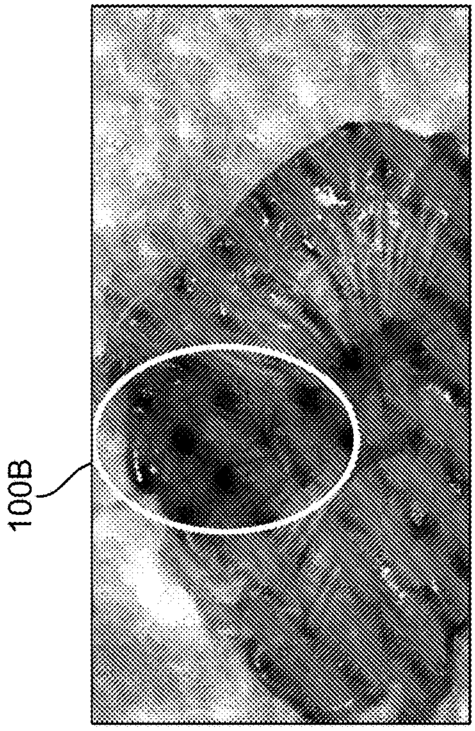
FIG. 10B shows an image of an unablated target tissue region injected overlaid with the determined perfusion property, per an embodiment herein.
Figure 10C:
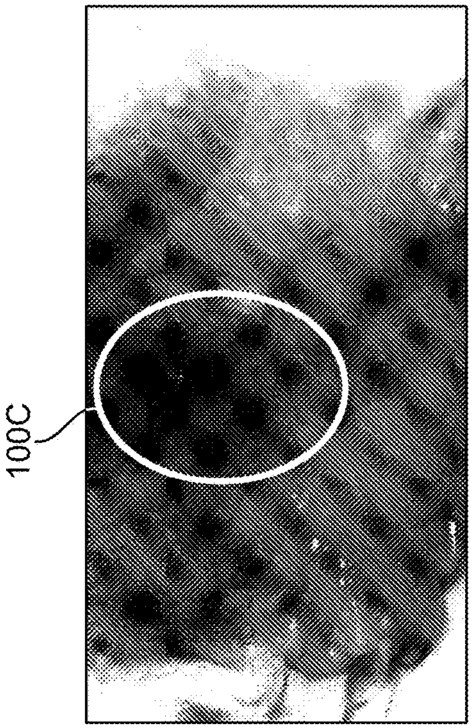
FIG. 10C shows an image of an ablated target tissue region injected with the ICG dye.
Figure 10D:
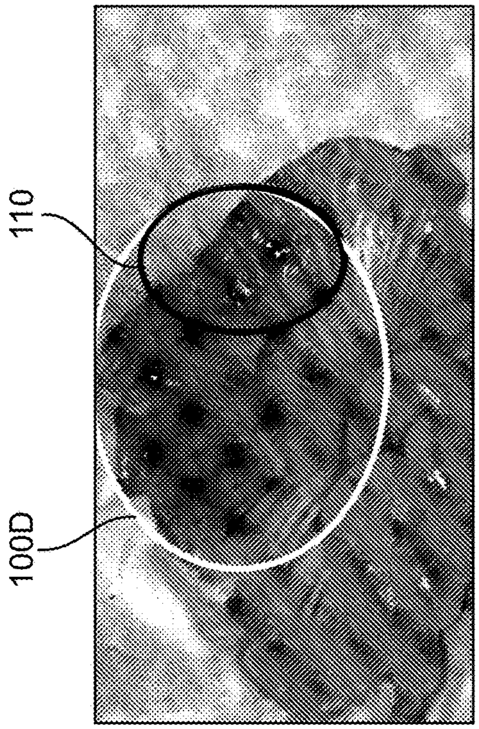
FIG. 10D shows an image of an ablated target tissue region injected overlaid with the determined perfusion property, per an embodiment herein.

Further, per FIGS. 10A-D the systems, methods, and media herein are more capable at determining areas of perfusion property than the currently available ICG dies. Although visualizations of an unablated target tissue with the ICG dye, per FIG. 10A, and via the instant methods, systems, and media, per FIG. 10B, show the same areas of reduced perfusion 100A and 100B, reduced perfusion area 100C of tissue visualized with the ICG dye, per FIG. 10C, is incapable of detecting areas of reduced perfusion induced by ablation. By contrast, per FIG. 10D, the methods, systems, and media herein are capable of detecting areas of reduced perfusion induced by ablation 110 in addition to the remaining areas of reduced perfusion 110D.

Figure 9C:
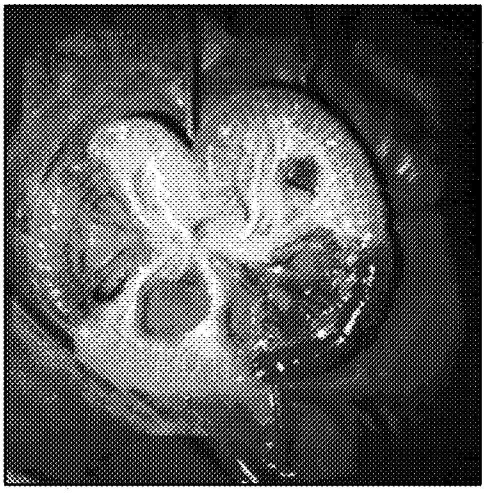
FIG. 9C shows an image of the target tissue region overlaid with the image of the perfusion within the target tissue region, per an embodiment herein.
Figure 9B:
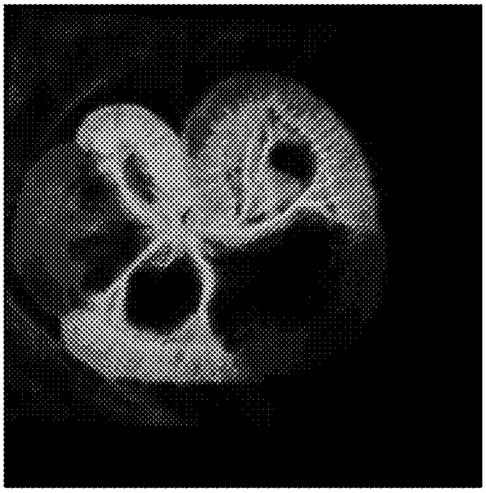
FIG. 9B shows an image of the perfusion within the target tissue region, per an embodiment herein.
Figure 9A:
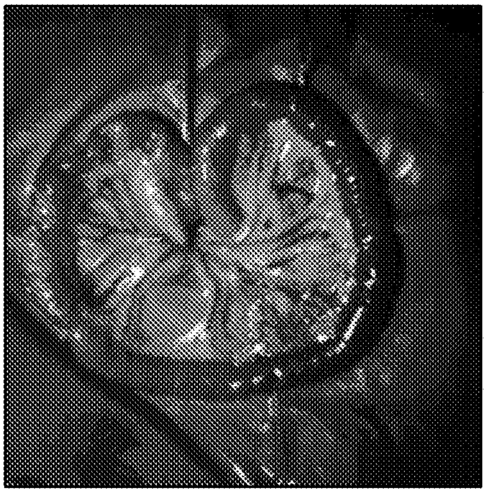
FIG. 9A shows another image of a target tissue region, per an embodiment herein.

In some embodiments, the perfusion property of the target tissue region is determined based at least on the set of images. In some embodiments, the perfusion measures a rate at which a fluid is delivered to tissue, or volume of the fluid per unit time per unit tissue mass in $m^3/(s\cdot kg)$ or ml/min/g. In some embodiments, the fluid is blood, sweat, semen, saliva, pus, urine, air, mucus, milk, bile, a hormone, or any combination thereof. In some embodiments, the perfusion property is further determined by measurements collected by an oximeter, a pulse rate monitor, or any combination thereof. In some embodiments, the perfusion property is further determined based on predetermined perfusion properties of an organ or tissue. FIG. 9A shows an exemplary image of a target tissue region. FIG. 9B shows an exemplary image of the perfusion of the target tissue region. FIG. 9C shows an exemplary image of the target tissue region overlaid with the image of the perfusion of the target tissue region. As seen, the ability to see the perfusion of the target tissue in addition to its image enables a surgical operator to determine areas with higher and lower perfusion to treat and/or avoid those portions the target tissue accordingly. Areas with higher perfusion normally indicate critical structures, which, if damaged during surgery, can be harmful or fatal to the patient. It is estimated that about 2% of hysterectomies result in complications due to such damage of critical structure, whereas such complications cost about 1 billion dollars to treat.

Spatial Measurements

In some embodiments, the set of spatial measurements of the target tissue region is determined based at least on the set of images. In some embodiments, the deformation of the target tissue region is determined based at least on the set of spatial measurements. In some embodiments, the images of the target tissue region comprise two-dimensional images of the target tissue region, wherein the set of spatial measurements of the target tissue region is determined based on the two-dimensional images of the target tissue region. In some embodiments, the images of the target tissue region comprise three-dimensional images of the target tissue region, wherein the set of spatial measurements of the target tissue region is determined based on the three-dimensional images of the target tissue region. In some embodiments, the set of spatial measurements of the target tissue region are two-dimensional. In some embodiments, the set of spatial measurements of the target tissue region are two-dimensional, wherein one dimension is normal to the target tissue region. In some embodiments, the set of spatial measurements of the target tissue region are three-dimensional.

Viscoelastic Property

In some embodiments, the viscoelastic property of the target tissue region is determined based at least on the deformation of the target tissue region, the perfusion property of the target tissue region, or both. In some embodiments, the viscoelastic property comprises a viscosity property, an elastic property, a fluid mechanics property, or any combination thereof. In some embodiments, the viscoelastic property comprises a stiffness. In some embodiments, the viscosity property correlates to a rate at which the target tissue deforms under force. In some embodiments, the elastic property correlates to the deformation distance under force. In some embodiments, the viscosity property is a kinematic viscosity, a dynamic viscosity, or both. In some embodiments, the fluid mechanics property is a flow resistance, a pulse rate, a fluid pressure, a fluid volume, a fluid temperature, a fluid density, or any combination thereof.

Types of Imaging

Figure 5A:
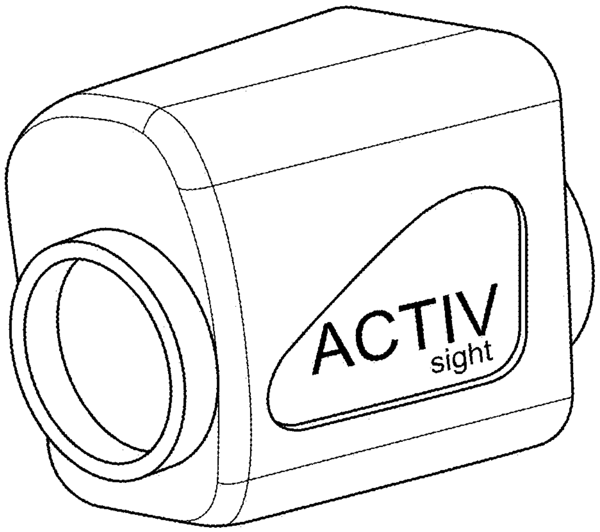
FIG. 5A shows an image of a device for obtaining a set of images of the target tissue region, per an embodiment herein.
Figure 5B:
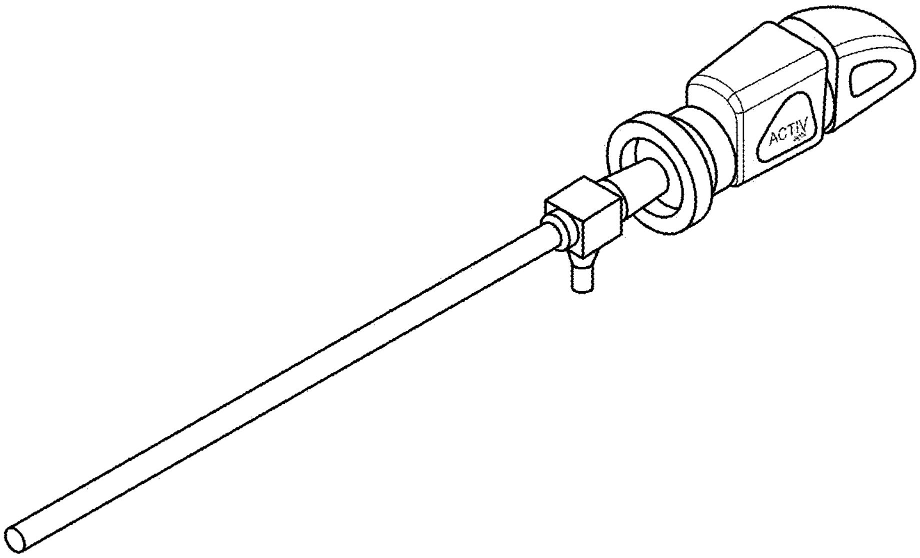
FIG. 5B shows an image of a device with a laparoscope for obtaining a set of images of the target tissue region, per an embodiment herein.
Figure 6:
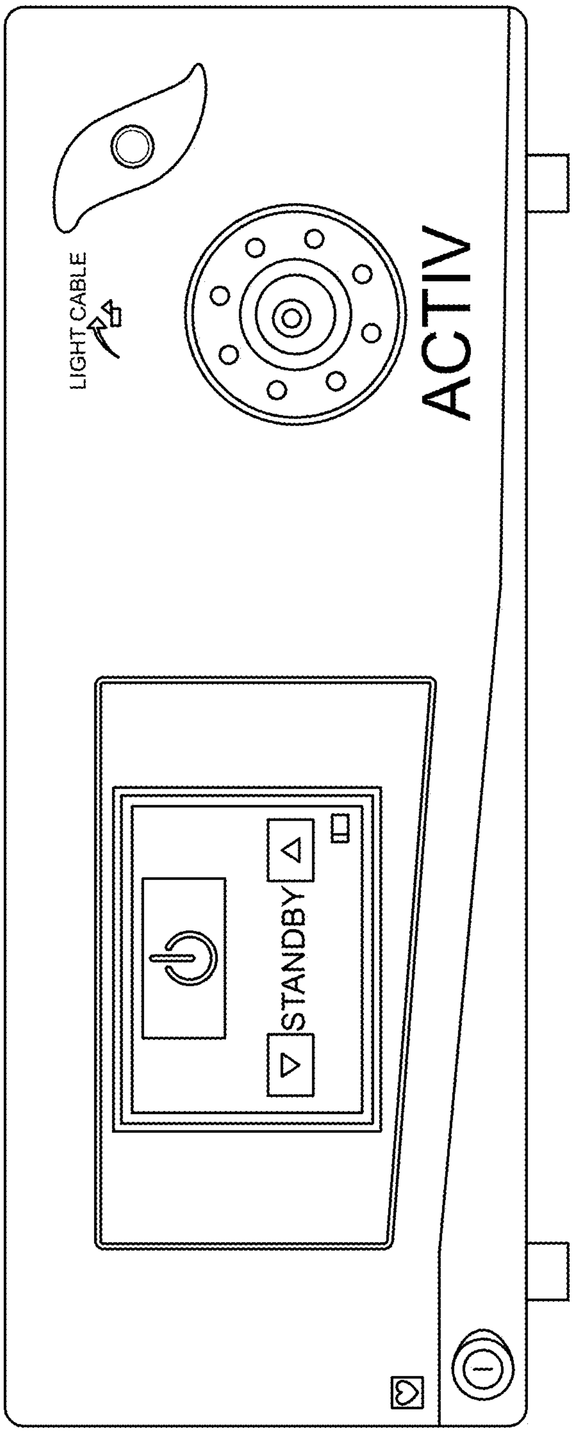
FIG. 6 shows an image of a connectivity device for transferring the set of images of the target tissue region, per an embodiment herein.
Figure 7:
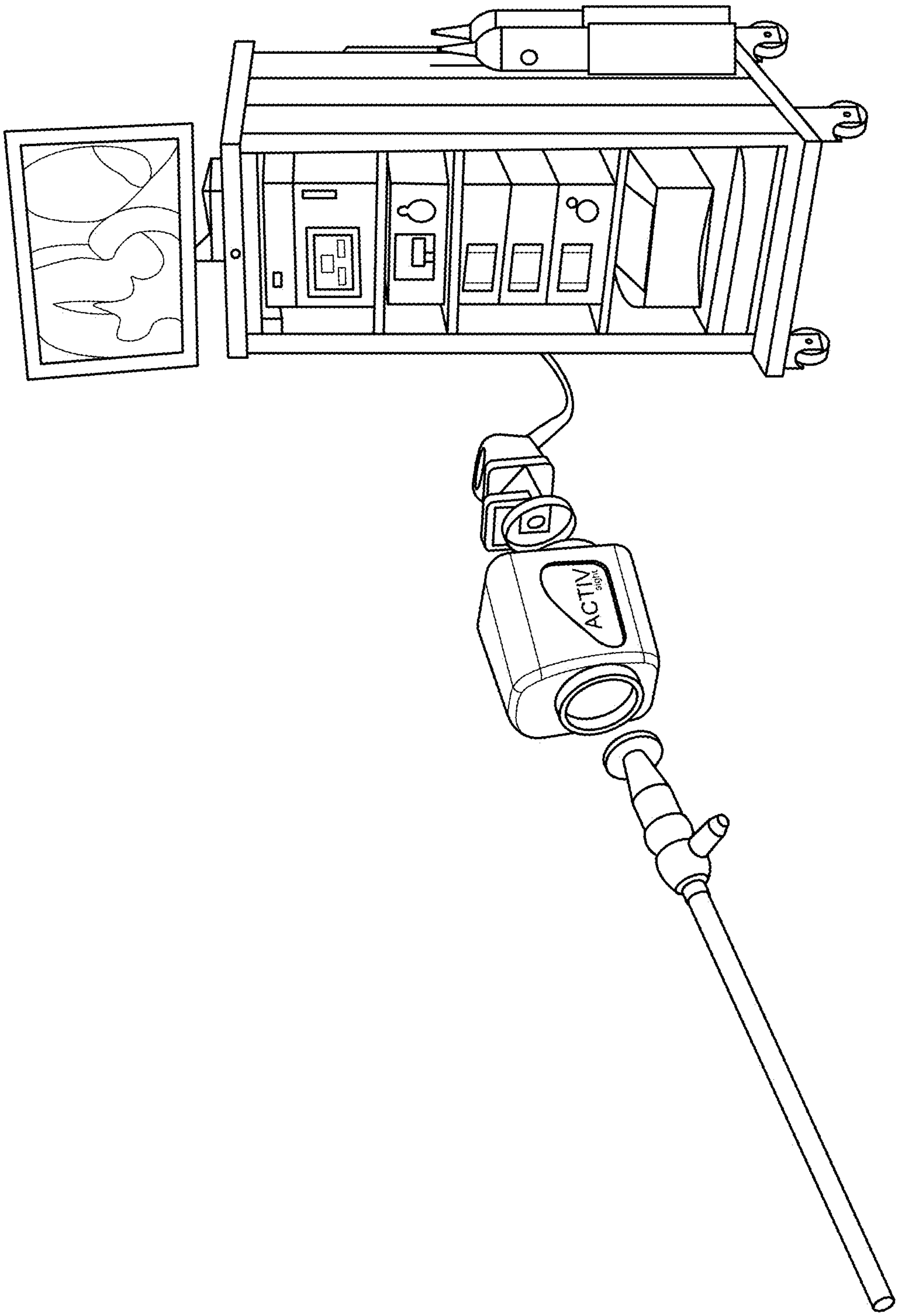
FIG. 7 shows an image of a system for collecting and transferring the set of images of the target tissue region, per an embodiment herein.

FIGS. 5A and 5B show images of a device for obtaining a set of images of the target tissue region, without and with a laparoscope, respectively. FIG. 6 shows an image of a connectivity device for transferring the set of images of the target tissue region. FIG. 7 shows an image of a system for collecting and transferring the set of images of the target tissue region In some embodiments, the set of images comprises a laser speckle image, a Red-Green-Blue (RGB) image, an RGB-Depth image, or any combination thereof. In some embodiments, the set of images comprises a laser speckle video, a Red-Green-Blue (RGB) video, an RGB-Depth video, or any combination thereof. In some embodiments, the RGB-Depth image comprises an RGB image overlaid with a depth measurement. In some embodiments, the laser speckle image is a subjective laser speckle image, an objective laser speckle image, a near-field laser speckle image, or any combination thereof. In some embodiments, a subjective laser speckle image is captured while the sample is directly illuminated the with a coherent light (e.g. a laser beam). In some embodiments, the subjective laser speckle image depends on the viewing system parameters, such as, for example: the size of the lens aperture, and the position of the imaging system. In some embodiments, a subjective laser speckle image is captured while the sample is indirectly illuminated the with a coherent light (e.g. a laser beam). In some embodiments, the laser speckle image is captured by a camera.

Figure 3:
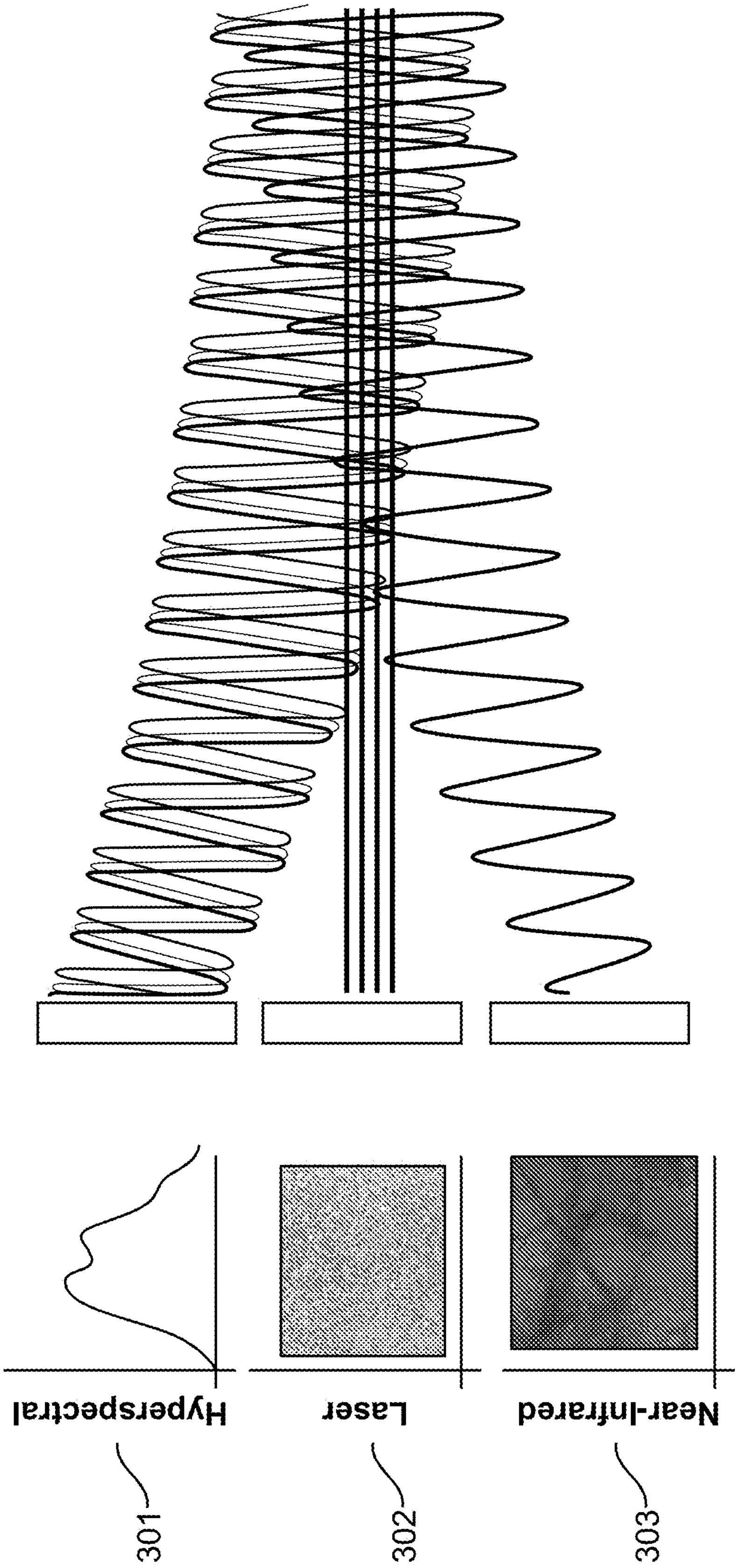
FIG. 3 shows a schematic diagram of various light frequencies, per an embodiment herein.
Figure 11:
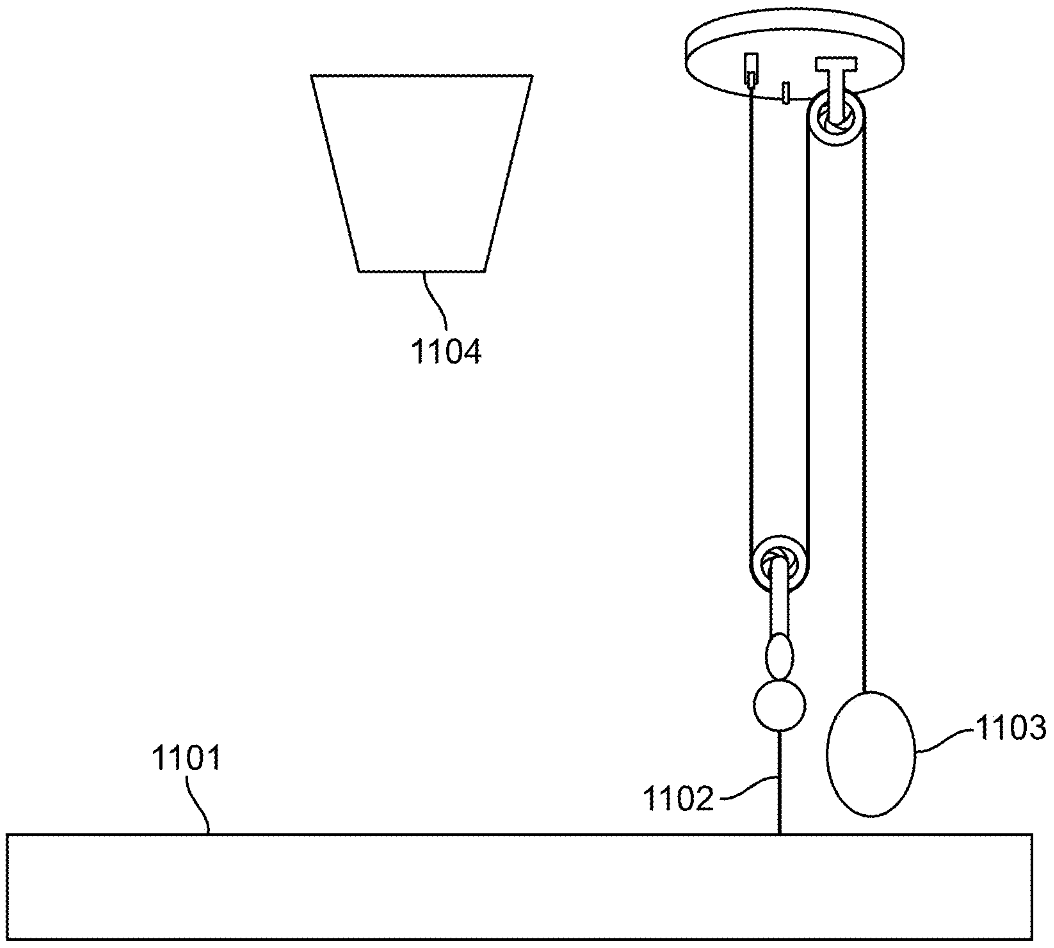
FIG. 11 shows an exemplary setup to capture a speckle image of a target tissue region undergoing a known deformation by a pre-determined force, per an embodiment herein.

In some embodiments, the set of images is obtained while emitting two or more different wavelengths of light at the target tissue region. In some embodiments, the set of images is obtained while emitting about 10 to about 1,000 different wavelengths of light at the target tissue region. In some embodiments, per FIG. 3, the set of images is obtained while emitting a hyperspectral combination of wavelengths 301, a laser wavelength 302, and a near-infrared wavelength 303. In some embodiments, the set of images of the target issue region and the set spatial measurements of the target tissue region are obtained simultaneously in real time. In some embodiments, the set of images of the target issue region and the set spatial measurements of the target tissue region are obtained simultaneously in real time as the target issue region undergoes the deformation. In some embodiments, the set of images of the target issue region is obtained in-vitro. In some embodiments, the set of images of the target issue region is obtained in-vivo. In some embodiments, at least one of the set of images of the target issue region is obtained while the target tissue region undergoes a known deformation by a pre-determined force. In some embodiments, a first image of the set of images of the target issue region is obtained while the target tissue region undergoes a known deformation by a pre-determined force. FIG. 11 shows an exemplary setup to capture a speckle image of the target issue region 1101 while the target tissue region 1101 undergoes a known deformation by a pre-determined force 1103. As shown, a thread 1102 is attached to the target tissue region 1101 imparting a known pre-determined force 1103 thereon, while a speckle image is captured by an image capturing device 1104. As shown therein, the thread 1102 imparts a normal tensile pre-determined force 1103 to the target tissue region 1101 via the thread 1102. Additionally or alternatively, the thread 1102 imparts a normal compressive, or a shear pre-determined force 1103 to the target tissue region 1101.

In some embodiments, the set of images are all captured with the same orientation between the image capturing device and the target tissue. In some embodiments, at least a portion of the set of images are all captured with the same orientation between the image capturing device and the target tissue.

Depth Measurements

In some embodiments, the method further comprises obtaining depth measurements from a depth sensor. In some embodiments, the depth sensor is a stereo triangulation sensor, a structured light sensor, a video camera, a time of flight sensor, an interferometer, a coded aperture, or any combination thereof. In some embodiments, the deformation of the target tissue region is further based on the depth measurements. In some embodiments, the spatial measurements are one-dimensional, two-dimensional, or three-dimensional. In some embodiments, the deformation of the target tissue region comprises a one-dimensional deformation, a two-dimensional deformation, a three-dimensional deformation, or any combination thereof.

Feedback

In some embodiments, the force is applied by a human operator. In some embodiments, the method further comprises providing a feedback to the operator. In some embodiments, the method further comprises providing a feedback to the operator based on the determined estimated force applied on the target tissue region. In some embodiments, the feedback comprises a visual feedback, an auditory feedback, a haptic feedback, or any combination thereof. In some embodiments, the visual feedback comprises a color coded visual feedback, a displayed value, a map, or any combination thereof corresponding to the estimated force. In some embodiments, a relationship between the estimated force and the feedback is linear, non-linear, or exponential.

In some embodiments, the force is applied by an autonomous or semi-autonomous device. In some embodiments, the method further comprises providing a control feedback to the autonomous or semi-autonomous device based on the force applied by the deformed tissue. In some embodiments, the autonomous or semi-autonomous device alters its treatment based on the control feedback.

Flow Rate and Identification

In some embodiments, the method further comprises determining a fluid flow rate within the target tissue. In some embodiments, the flow rate is based at least on (i) the set of images, (ii) the spatial measurements, (iii) the viscoelastic property of the target tissue region, (iv) the deformation of the target tissue region, or any combination thereof. In some embodiments, the fluid is blood, sweat, semen, saliva, pus, urine, air, mucus, milk, bile, a hormone, or any combination thereof. In some embodiments, the fluid flow rate within the target tissue is determined by a machine learning algorithm. In some embodiments, the fluid flow rate is determined by a machine learning algorithm. In some embodiments, the method further comprises determining an identification of the target tissue based at least on (i) the set of images, (ii) the spatial measurements, (iii) the viscoelastic property of the target tissue region, (iv) the deformation of the target tissue region, or any combination thereof. In some embodiments, the identification of the target tissue is determined by a machine learning algorithm. In some embodiments, the identification of the target tissue is an identification that the target tissue is cancerous, benign, malignant, or healthy.

Machine Learning

In some embodiments, determining the mechanical property, the viscoelastic property, or both of the target tissue region is performed by a machine learning algorithm. In some embodiments, determining the estimated force applied to the target tissue region is performed by a machine learning algorithm. In some embodiments, the machine learning algorithm employs a neural network.

Examples of the machine learning algorithms that can be used with the embodiments herein may comprise a regression-based learning algorithm, linear or non-linear algorithms, feed-forward neural network, generative adversarial network (GAN), or deep residual networks. The machine learning algorithm may include, for example, an unsupervised learning classifier, a supervised learning classifier, or a combination thereof. An unsupervised learning classifier may include, for example, clustering, hierarchical clustering, k-means, mixture models, DBSCAN, OPTICS algorithm, anomaly detection, local outlier factor, neural networks, autoencoders, deep belief nets, hebbian learning, generative adversarial networks, self-organizing map, expectation-maximization algorithm (EM), method of moments, blind signal separation techniques, principal component analysis, independent component analysis, non-negative matrix factorization, singular value decomposition, or a combination thereof. A supervised learning classifier may include, for example, support vector machines, linear regression, logistic regression, linear discriminant analysis, decision trees, k-nearest neighbor algorithm, neural networks, similarity learning, or a combination thereof. In some embodiments, the machine learning algorithm may comprise a deep learning neural network. The deep learning neural network may comprise a convolutional neural network (CNN). The CNN may include, for example, U-Net, ImageNet, LeNet-5, AlexNet, ZFNet, GoogleNet, VGGNet, ResNet18 or ResNet, etc.

Figure 4:
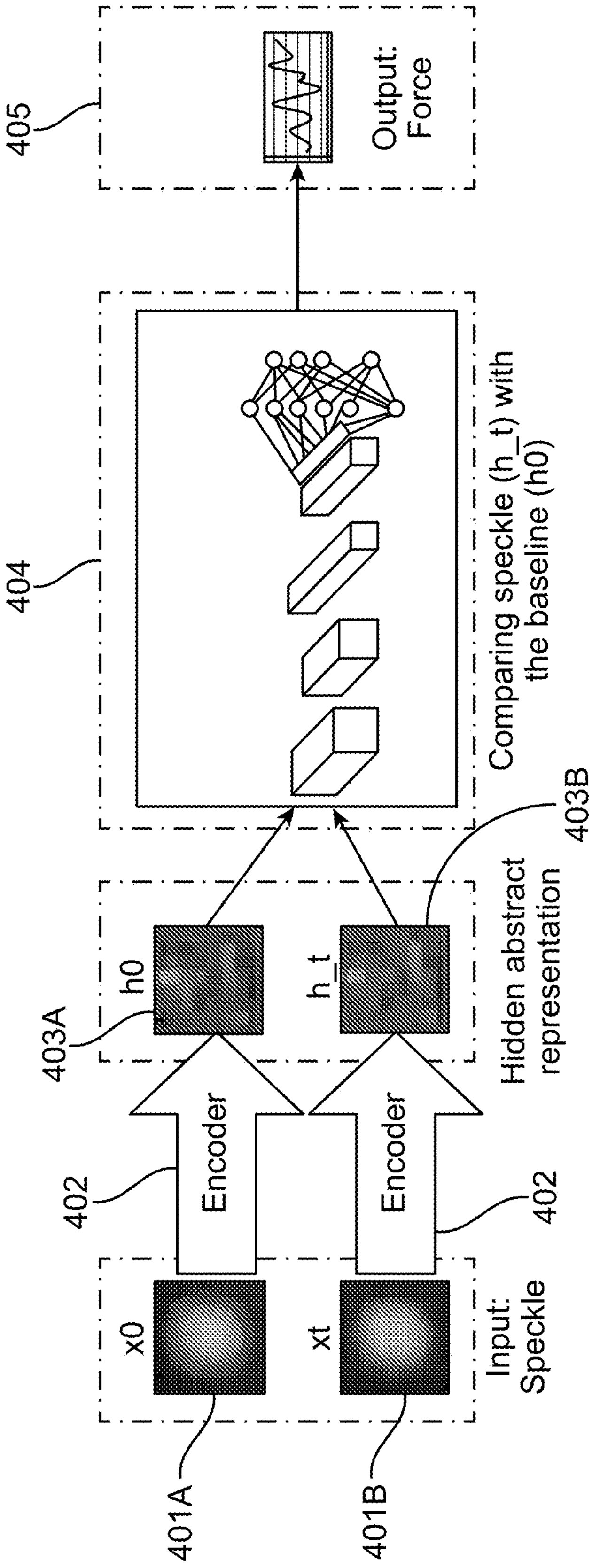
FIG. 4 shows a schematic diagram of a machine learning algorithm to determine a viscoelastic property of a target issue region, per an embodiment herein.

FIG. 4 shows an exemplary schematic flowchart of a machine learning algorithm for determining the estimated force applied to the target tissue region. As shown, the exemplary algorithm comprises: receiving a first input speckle (x0) 401A and a second input speckle (xt) 401B; determining a hidden abstract representation of the first input speckle (h0) 403A and second input speckle (h_t) 403B via an encoder 402, comparing the abstract representations of the first (h0) and second input speckles (h_t) 404; and determining an output force 405. In some embodiments, at least one of the first input speckle (h0) 403A and the second input speckle (h_t) 403B are captured while a predetermined force is applied to the target tissue region. As changes between two or more speckle images can be caused by a motion artifact of the tissue, fluid flow therein, or external forces, the predetermined force applied during one or more of the speckle images, and the determined perfusion property, enables the machine learning algorithms herein to differentiate changes in the viscoelastic properties of the target tissue region in subsequent speckle images.

In some embodiments, the machine learning algorithm is a supervised machine learning algorithm. In some embodiments, the machine learning algorithms utilized therein employ one or more forms of labels including but not limited to human annotated labels and semi-supervised labels. The human annotated labels can be provided by a hand-crafted heuristic. For example, the hand-crafted heuristic can comprise examining differences between images of the target tissue region, spatial measurements, or both. The semi-supervised labels can be determined using a clustering technique to find images of the target tissue region, spatial measurements, or both similar to those flagged by previous human annotated labels and previous semi-supervised labels. The semi-supervised labels can employ a XGBoost, a neural network, or both.

The distant supervision method can create a large training set seeded by a small hand-annotated training set. The distant supervision method can comprise positive-unlabeled learning with the training set as the 'positive' class. The distant supervision method can employ a logistic regression model, a recurrent neural network, or both. The recurrent neural network can be advantageous for Natural Language Processing (NLP) machine learning.

Examples of machine learning algorithms can include a support vector machine (SVM), a naïve Bayes classification, a random forest, a neural network, deep learning, or other supervised learning algorithm or unsupervised learning algorithm for classification and regression. The machine learning algorithms can be trained using one or more training datasets.

In some embodiments, the machine learning algorithm utilizes regression modeling, wherein relationships between predictor variables and dependent variables are determined and weighted. In one embodiment, for example the viscoelastic property can be a dependent variable and is derived from the images of the target tissue region, spatial measurements, or both.

In some embodiments, a machine learning algorithm is used to select catalogue images and recommend project scope. A non-limiting example of a multi-variate linear regression model algorithm is seen below: probability=$A_0$+$A_1(X_1)$+$A_2(X_2)$+$A_3(X_3)$+$A_4(X_4)$+$A_5(X_5)$+$A_6(X_6)$+$A_7(X_7)$ . . . wherein $A_i$ ($A_1$, $A_2$, $A_3$, $A_4$, $A_5$, $A_6$, $A_7$, . . . ) are "weights" or coefficients found during the regression modeling; and $X_i$ ($X_1$, $X_2$, $X_3$, $X_4$, $X_5$, $X_6$, $X_7$, . . . ) are data collected from the User. Any number of $A_i$ and $X_i$ variable can be included in the model. For example, in a non-limiting example wherein there are 7 $X_i$ terms, $X_1$ is the number of images, $X_2$ is the number of spatial measurement, and $X_3$ is the viscoelastic property of the target tissue region. In some embodiments, the programming language "R" is used to run the model.]

In some embodiments, training comprises multiple steps. In a first step, an initial model is constructed by assigning probability weights to predictor variables. In a second step, the initial model is used to "recommend" the viscoelastic property of the target tissue region. In a third step, the validation module accepts verified data regarding the viscoelastic property of the target tissue region and feeds back the verified data to the renovation probability calculation. At least one of the first step, the second step, and the third step can repeat one or more times continuously or at set intervals.

Method for Training a Neural Network

Figure 2:
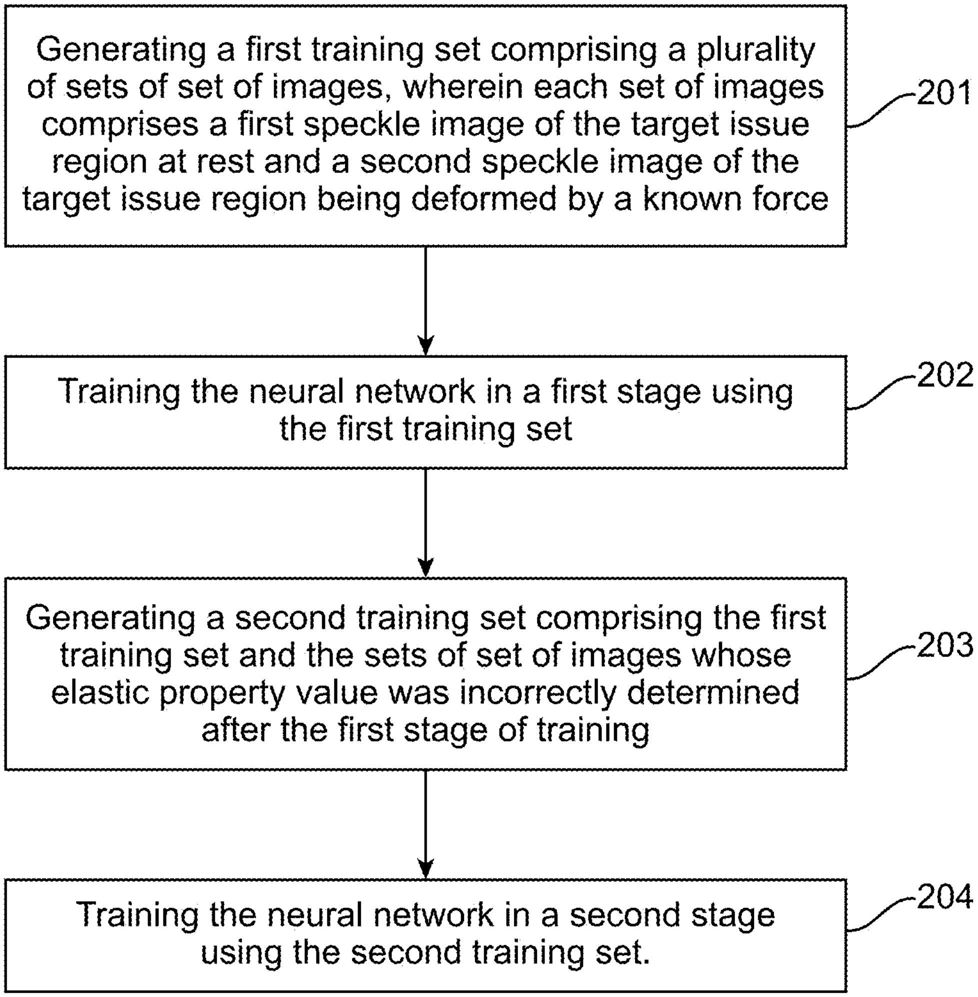
FIG. 2 shows a schematic diagram of a method for training a neural network to determine a viscoelastic property of a target issue region, per an embodiment herein.

Another aspect provided herein is a computer-implemented method for training a neural network to determine an elastic property of a target issue region. In some embodiments, per FIG. 2, the method comprises: generating a first training set 201; training the neural network in a first stage using the first training set 202; generating a second training set 203; and training the neural network in a second stage using the second training set 204.

In some embodiments, the first training set comprising a plurality of sets of set of images. In some embodiments, each set of images comprises a first speckle image of the target issue region at rest and a second speckle image of the target issue region. In some embodiments, the second speckle image is captured while the target issue region is being deformed. In some embodiments, the second speckle image is captured while the target issue region is being deformed by a known force. In some embodiments, the second training set comprising the first training set and the sets of set of images whose elastic property value was incorrectly determined after the first stage of training.

In some embodiments, the set of images comprises a subjective set of images, an objective set of images, a near-field set of images, or any combination thereof. In some embodiments, the set of images is obtained while emitting at least 10 different wavelengths of light at the target tissue region. In some embodiments, the set of images is obtained while emitting about 10 to about 1,000 different wavelengths of light at the target tissue region. In some embodiments, the viscoelastic property comprises a viscous property, an elastic property, a fluid mechanics property, or any combination thereof. In some embodiments, the spatial measurements are one-dimensional, two-dimensional, or three-dimensional.

Alternative Embodiments

In another aspect, the present disclosure provides a method of tracking tissue deformations. The method may comprise: (a) obtaining a scalar optical flow reading, wherein the scalar optical flow reading corresponds to one or more laser speckle signals; (b) using said scalar optical flow reading to determine a pixel-wise motion magnitude estimate for a tissue region; and (c) integrating said pixel-wise motion magnitude estimate over time and space to track a deformation of the tissue region. In some embodiments, the one or more laser speckle signals may be associated with, based on, and/or derived from the deformation of the tissue region. In some embodiments, the one or more laser speckle signals may be obtained during a deformation of the tissue region. In some embodiments, the pixel-wise motion magnitude estimate may comprise a directionless motion estimate. In some cases, the method may further comprise combining (i) the pixel-wise motion estimate with (ii) depth and/or RGB-D data of the tissue region to generate a pixel-wise displacement map. The pixel-wise displacement map may comprise a visual or data-based representation of a deformation of a tissue region at one or more pixels (or per pixel of an image of the tissue region).

Terms and Definitions

Unless otherwise defined, all technical terms used herein have the same meaning as commonly understood by one of ordinary skill in the art to which this disclosure belongs.

As used herein, the singular forms "a," "an," and "the" include plural references unless the context clearly dictates otherwise. Any reference to "or" herein is intended to encompass "and/or" unless otherwise stated.

As used herein, the term "about" in some cases refers to an amount that is approximately the stated amount.

As used herein, the term "about" refers to an amount that is near the stated amount by 10%, 5%, or 1%, including increments therein.

As used herein, the term "about" in reference to a percentage refers to an amount that is greater or less the stated percentage by 10%, 5%, or 1%, including increments therein.

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

As used herein, the term "perfusion" refers to is a measurement of the passage of fluid through an organ or a tissue. In some embodiments, perfusion is measured as the rate at which blood is delivered to tissue, or volume of blood per unit time (blood flow) per unit tissue mass. In some embodiments, perfusion is measured in $m^3/(s \cdot kg)$ or ml/min/g.

As used herein, the term "speckle image" refers to a pattern is produced by the mutual interference of a set of incoherent waves. In some embodiments, the waves have the same frequency, having different phases and amplitudes, which add together to give a resultant wave whose amplitude varies randomly.

Computing System

Figure 12:
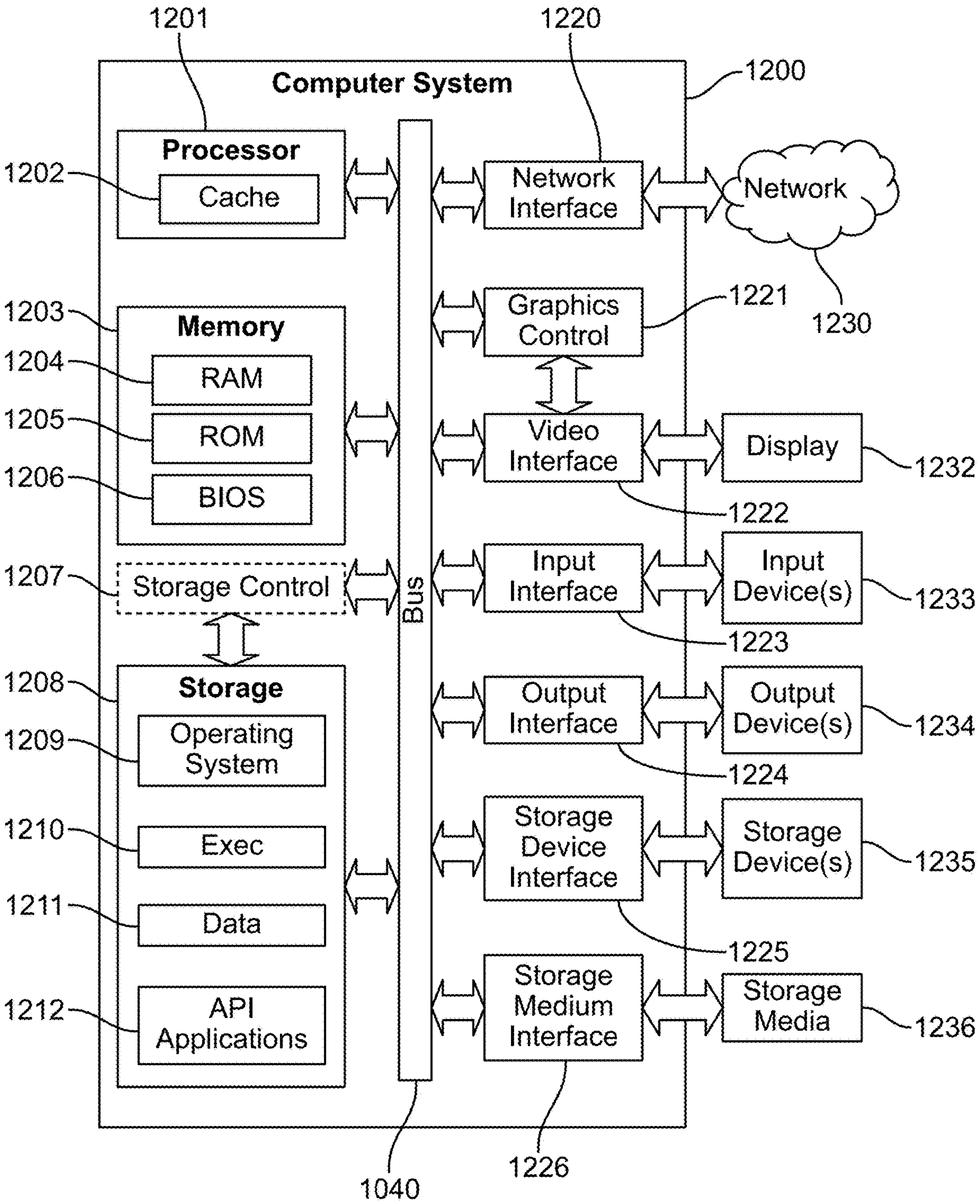
FIG. 12 shows a non-limiting example of a computing device; in this case, a device with one or more processors, memory, storage, and a network interface, per an embodiment herein.

Referring to FIG. 12, a block diagram is shown depicting an exemplary machine that includes a computer system 1200 (e.g., a processing or computing system) within which a set of instructions can execute for causing a device to perform or execute any one or more of the aspects and/or methodologies for static code scheduling of the present disclosure. The components in FIG. 12 are examples only and do not limit the scope of use or functionality of any hardware, software, embedded logic component, or a combination of two or more such components implementing particular embodiments.

Computer system 1200 may include one or more processors 1201, a memory 1203, and a storage 1208 that communicate with each other, and with other components, via a bus 1240. The bus 1240 may also link a display 1232, one or more input devices 1233 (which may, for example, include a keypad, a keyboard, a mouse, a stylus, etc.), one or more output devices 1234, one or more storage devices 1235, and various tangible storage media 1236. All of these elements may interface directly or via one or more interfaces or adaptors to the bus 1240. For instance, the various tangible storage media 1236 can interface with the bus 1240 via storage medium interface 1226. Computer system 1200 may have any suitable physical form, including but not limited to one or more integrated circuits (ICs), printed circuit boards (PCBs), mobile handheld devices (such as mobile telephones or PDAs), laptop or notebook computers, distributed computer systems, computing grids, or servers.

Computer system 1200 includes one or more processor(s) 1201 (e.g., central processing units (CPUs) or general purpose graphics processing units (GPGPUs)) that carry out functions. Processor(s) 1201 optionally contains a cache memory unit 1202 for temporary local storage of instructions, data, or computer addresses. Processor(s) 1201 are configured to assist in execution of computer readable instructions. Computer system 1200 may provide functionality for the components depicted in FIG. 12 as a result of the processor(s) 1201 executing non-transitory, processor-executable instructions embodied in one or more tangible computer-readable storage media, such as memory 1203, storage 1208, storage devices 1235, and/or storage medium 1236. The computer-readable media may store software that implements particular embodiments, and processor(s) 1201 may execute the software. Memory 1203 may read the software from one or more other computer-readable media (such as mass storage device(s) 1235, 1236) or from one or more other sources through a suitable interface, such as network interface 1220. The software may cause processor(s) 1201 to carry out one or more processes or one or more steps of one or more processes described or illustrated herein. Carrying out such processes or steps may include defining data structures stored in memory 1203 and modifying the data structures as directed by the software.

The memory 1203 may include various components (e.g., machine readable media) including, but not limited to, a random access memory component (e.g., RAM 1204) (e.g., static RAM (SRAM), dynamic RAM (DRAM), ferroelectric random access memory (FRAM), phase-change random access memory (PRAM), etc.), a read-only memory component (e.g., ROM 1205), and any combinations thereof. ROM 1205 may act to communicate data and instructions unidirectionally to processor(s) 1201, and RAM 1204 may act to communicate data and instructions bidirectionally with processor(s) 1201. ROM 1205 and RAM 1204 may include any suitable tangible computer-readable media described below. In one example, a basic input/output system 1206 (BIOS), including basic routines that help to transfer information between elements within computer system 1200, such as during start-up, may be stored in the memory 1203.

Fixed storage 1208 is connected bidirectionally to processor(s) 1201, optionally through storage control unit 1207. Fixed storage 1208 provides additional data storage capacity and may also include any suitable tangible computer-readable media described herein. Storage 1208 may be used to store operating system 1209, executable(s) 1210, data 1211, applications 1212 (application programs), and the like. Storage 1208 can also include an optical disk drive, a solid-state memory device (e.g., flash-based systems), or a combination of any of the above. Information in storage 1208 may, in appropriate cases, be incorporated as virtual memory in memory 1203.

In one example, storage device(s) 1235 may be removably interfaced with computer system 1200 (e.g., via an external port connector (not shown)) via a storage device interface 1225. Particularly, storage device(s) 1235 and an associated machine-readable medium may provide non-volatile and/or volatile storage of machine-readable instructions, data structures, program modules, and/or other data for the computer system 1200. In one example, software may reside, completely or partially, within a machine-readable medium on storage device(s) 1235. In another example, software may reside, completely or partially, within processor(s) 1201.

Bus 1240 connects a wide variety of subsystems. Herein, reference to a bus may encompass one or more digital signal lines serving a common function, where appropriate. Bus 1240 may be any of several types of bus structures including, but not limited to, a memory bus, a memory controller, a peripheral bus, a local bus, and any combinations thereof, using any of a variety of bus architectures. As an example and not by way of limitation, such architectures include an Industry Standard Architecture (ISA) bus, an Enhanced ISA (EISA) bus, a Micro Channel Architecture (MCA) bus, a Video Electronics Standards Association local bus (VLB), a Peripheral Component Interconnect (PCI) bus, a PCI-Express (PCI-X) bus, an Accelerated Graphics Port (AGP) bus, HyperTransport (HTX) bus, serial advanced technology attachment (SATA) bus, and any combinations thereof.

Computer system 1200 may also include an input device 1233. In one example, a user of computer system 1200 may enter commands and/or other information into computer system 1200 via input device(s) 1233. Examples of an input device(s) 1233 include, but are not limited to, an alpha-numeric input device (e.g., a keyboard), a pointing device (e.g., a mouse or touchpad), a touchpad, a touch screen, a multi-touch screen, a joystick, a stylus, a gamepad, an audio input device (e.g., a microphone, a voice response system, etc.), an optical scanner, a video or still image capture device (e.g., a camera), and any combinations thereof. In some embodiments, the input device is a Kinect, Leap Motion, or the like. Input device(s) 1233 may be interfaced to bus 1240 via any of a variety of input interfaces 1223 (e.g., input interface 1223) including, but not limited to, serial, parallel, game port, USB, FIREWIRE, THUNDERBOLT, or any combination of the above.

In particular embodiments, when computer system 1200 is connected to network 1230, computer system 1200 may communicate with other devices, specifically mobile devices and enterprise systems, distributed computing systems, cloud storage systems, cloud computing systems, and the like, connected to network 1230. Communications to and from computer system 1200 may be sent through network interface 1220. For example, network interface 1220 may receive incoming communications (such as requests or responses from other devices) in the form of one or more packets (such as Internet Protocol (IP) packets) from network 1230, and computer system 1200 may store the incoming communications in memory 1203 for processing. Computer system 1200 may similarly store outgoing communications (such as requests or responses to other devices) in the form of one or more packets in memory 1203 and communicated to network 1230 from network interface 1220. Processor(s) 1201 may access these communication packets stored in memory 1203 for processing.

Examples of the network interface 1220 include, but are not limited to, a network interface card, a modem, and any combination thereof. Examples of a network 1230 or network segment 1230 include, but are not limited to, a distributed computing system, a cloud computing system, a wide area network (WAN) (e.g., the Internet, an enterprise network), a local area network (LAN) (e.g., a network associated with an office, a building, a campus or other relatively small geographic space), a telephone network, a direct connection between two computing devices, a peer-to-peer network, and any combinations thereof. A network, such as network 1230, may employ a wired and/or a wireless mode of communication. In general, any network topology may be used.

Information and data can be displayed through a display 1232. Examples of a display 1232 include, but are not limited to, a cathode ray tube (CRT), a liquid crystal display (LCD), a thin film transistor liquid crystal display (TFT-LCD), an organic liquid crystal display (OLED) such as a passive-matrix OLED (PMOLED) or active-matrix OLED (AMOLED) display, a plasma display, and any combinations thereof. The display 1232 can interface to the processor(s) 1201, memory 1203, and fixed storage 1208, as well as other devices, such as input device(s) 1233, via the bus 1240. The display 1232 is linked to the bus 1240 via a video interface 1222, and transport of data between the display 1232 and the bus 1240 can be controlled via the graphics control 1221. In some embodiments, the display is a video projector. In some embodiments, the display is a head-mounted display (HMD) such as a VR headset. In further embodiments, suitable VR headsets include, by way of non-limiting examples, HTC Vive, Oculus Rift, Samsung Gear VR, Microsoft HoloLens, Razer OSVR, FOVE VR, Zeiss VR One, Avegant Glyph, Freefly VR headset, and the like. In still further embodiments, the display is a combination of devices such as those disclosed herein.

In addition to a display 1232, computer system 1200 may include one or more other peripheral output devices 1234 including, but not limited to, an audio speaker, a printer, a storage device, and any combinations thereof. Such peripheral output devices may be connected to the bus 1240 via an output interface 1224. Examples of an output interface 1224 include, but are not limited to, a serial port, a parallel connection, a USB port, a FIREWIRE port, a THUNDERBOLT port, and any combinations thereof.

In addition, or as an alternative, computer system 1200 may provide functionality as a result of logic hardwired or otherwise embodied in a circuit, which may operate in place of or together with software to execute one or more processes or one or more steps of one or more processes described or illustrated herein. Reference to software in this disclosure may encompass logic, and reference to logic may encompass software. Moreover, reference to a computer-readable medium may encompass a circuit (such as an IC) storing software for execution, a circuit embodying logic for execution, or both, where appropriate. The present disclosure encompasses any suitable combination of hardware, software, or both; and Those of skill in the art will appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by one or more processor(s), or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In accordance with the description herein, suitable computing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will also recognize that select televisions, video players, and digital music players with optional computer network connectivity are suitable for use in the system described herein. Suitable tablet computers, in various embodiments, include those with booklet, slate, and convertible configurations, known to those of skill in the art.

In some embodiments, the computing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smartphone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®. Those of skill in the art will also recognize that suitable media streaming device operating systems include, by way of non-limiting examples, Apple TV®, Roku®, Boxee®, Google TV®, Google Chromecast®, Amazon Fire®, and Samsung® HomeSync®. Those of skill in the art will also recognize that suitable video game console operating systems include, by way of non-limiting examples, Sony® PS3®, Sony® PS4®, Microsoft® Xbox 360®, Microsoft Xbox One, Nintendo® Wii®, Nintendo® Wii U®, and Ouya®.

Non-Transitory Computer Readable Storage Medium

In some embodiments, the platforms, systems, media, and methods disclosed herein include one or more non-transitory computer readable storage media encoded with a program including instructions executable by the operating system of an optionally networked computing device. In further embodiments, a computer readable storage medium is a tangible component of a computing device. In still further embodiments, a computer readable storage medium is optionally removable from a computing device. In some embodiments, a computer readable storage medium includes, by way of non-limiting examples, CD-ROMs, DVDs, flash memory devices, solid state memory, magnetic disk drives, magnetic tape drives, optical disk drives, distributed computing systems including cloud computing systems and services, and the like. In some cases, the program and instructions are permanently, substantially permanently, semi-permanently, or non-transitorily encoded on the media.

Computer Program

In some embodiments, the platforms, systems, media, and methods disclosed herein include at least one computer program, or use of the same. A computer program includes a sequence of instructions, executable by one or more processor(s) of the computing device's CPU, written to perform a specified task. Computer readable instructions may be implemented as program modules, such as functions, objects, Application Programming Interfaces (APIs), computing data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Software Modules

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on a distributed computing platform such as a cloud computing platform. In some embodiments, software modules are hosted on one or more machines in one location. In other embodiments, software modules are hosted on one or more machines in more than one location.

Databases

In some embodiments, the platforms, systems, media, and methods disclosed herein include one or more databases, or use of the same. In view of the disclosure provided herein, those of skill in the art will recognize that many databases are suitable for storage and retrieval of image, flow rate, force, elastic, perfusion, viscoelastic information, or any combination thereof. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In a particular embodiment, a database is a distributed database. In other embodiments, a database is based on one or more local computer storage devices.

What is claimed is:

1. A computer-implemented method for training a neural network to determine a viscoelastic property of a target tissue region, the method comprising:

generating a first training set including a plurality of sets of images, wherein each set of images includes a first speckle image of the target tissue region at rest and a second speckle image of the target tissue region deformed by a known force;

training the neural network in a first stage using the first training set;

generating a second training set including the first training set and one or more sets of images having an elastic property value incorrectly determined after the first stage of training; and training the neural network in a second stage using the second training set.

2. The method of claim 1, wherein the sets of images comprise a subjective set of images, an objective set of images, a near-field set of images, or any combination thereof.

3. The method of claim 1, wherein generating the first training set including the plurality of sets of images comprises capturing the second speckle image while the target tissue region is being deformed.

4. The method of claim 1, wherein the viscoelastic property of the target tissue region is determined based at least on the deformation of the target tissue region.

5. The method of claim 1, wherein the viscoelastic property comprises a viscosity property, an elastic property, a fluid mechanics property, or any combination thereof.

6. The method of claim 5, wherein the viscosity property comprises a stiffness.

7. The method of claim 5, wherein the viscosity property correlates to a rate at which the target tissue deforms under force.

8. The method of claim 5, wherein the viscosity property comprises a kinematic viscosity, a dynamic viscosity, or both.

9. The method of claim 5, wherein the elastic property correlates to a deformation distance under force.

10. The method of claim 5, wherein the fluid mechanics property comprises a flow resistance, a pulse rate, a fluid pressure, a fluid volume, a fluid temperature, a fluid density, or any combination thereof.

11. The method of claim 1, wherein a set of spatial measurements of the target tissue region is determined based at least on the sets of images.

12. The method of claim 11, wherein the spatial measurements are one-dimensional, two-dimensional, or three-dimensional.

13. A computer-implemented system comprising:

a digital processing device including at least one processor, an operating system configured to perform executable instructions, a memory, and a computer program including instructions executable by the digital processing device to create an application for training a neural network to determine a viscoelastic property of a target tissue region, the instructions executable to:

generate a first training set including a plurality of sets of images, wherein each set of images includes a first speckle image of the target tissue region at rest and a second speckle image of the target tissue region deformed by a known force;

train the neural network in a first stage using the first training set;

generate a second training set including the first training set and one or more sets of images having an elastic property value incorrectly determined after the first stage of training; and train the neural network in a second stage using the second training set.

14. The system of claim 13, wherein the sets of images comprise a subjective set of images, an objective set of images, a near-field set of images, or any combination thereof.

15. The system of claim 13, wherein the instructions executable to generate the first training set including the plurality of sets of images further comprise instructions executable to capture the second speckle image while the target tissue region is being deformed.

16. The system of claim 13, wherein the viscoelastic property of the target tissue region is determined based at least on the deformation of the target tissue region.

17. The system of claim 13, wherein the viscoelastic property comprises a viscosity property, an elastic property, a fluid mechanics property, or any combination thereof.

18. A non-transitory computer-readable storage media encoded with a computer program including instructions executable by a processor to create an application for training a neural network to determine a viscoelastic property of a target tissue region, the instructions executable to:

generate a first training set including a plurality of sets of images, wherein each set of images includes a first speckle image of the target tissue region at rest and a second speckle image of the target tissue region deformed by a known force;

train the neural network in a first stage using the first training set;

generate a second training set including the first training set and one or more sets of images having an elastic property value incorrectly determined after the first stage of training; and train the neural network in a second stage using the second training set.

19. The media of claim 18, wherein the sets of images comprise a subjective set of images, an objective set of images, a near-field set of images, or any combination thereof.

20. The media of claim 18, wherein the viscoelastic property of the target tissue region is determined based at least on the deformation of the target tissue region.

* * * * *